United States Patent
Kohm et al.

(10) Patent No.: US 8,114,131 B2
(45) Date of Patent: Feb. 14, 2012

(54) EXTENSION LIMITING DEVICES AND METHODS OF USE FOR THE SPINE

(75) Inventors: Andrew Kohm, San Mateo, CA (US); Hugues F. Malandain, Mountain View, CA (US)

(73) Assignee: Kyphon SARL, Neuchatel (CH)

( * ) Notice: Subject to any disclaimer, the term of this patent is extended or adjusted under 35 U.S.C. 154(b) by 612 days.

(21) Appl. No.: 12/265,419

(22) Filed: Nov. 5, 2008

(65) Prior Publication Data

US 2010/0114166 A1    May 6, 2010

(51) Int. Cl.
*A61B 17/70* (2006.01)

(52) U.S. Cl. ...... 606/248; 606/249; 606/279; 623/17.11

(58) Field of Classification Search .......... 606/246–249; 623/17.11–17.16
See application file for complete search history.

(56) References Cited

U.S. PATENT DOCUMENTS

| | | |
|---|---|---|
| 0,624,969 A | 5/1899 | Peterson |
| 1,153,797 A | 9/1915 | Kegreisz |
| 1,516,347 A | 11/1924 | Pataky |
| 1,870,942 A | 8/1932 | Beatty |
| 2,077,804 A | 4/1937 | Morrison |
| 2,248,054 A | 7/1941 | Becker |
| 2,299,308 A | 10/1942 | Creighton |
| 2,472,103 A | 6/1949 | Giesen |
| 2,485,531 A | 10/1949 | Dzus et al. |
| 2,607,370 A | 8/1952 | Anderson |
| 2,677,369 A | 5/1954 | Knowles |
| 2,685,877 A | 8/1954 | Dobelle |
| 3,065,659 A | 11/1962 | Eriksson et al. |
| 3,108,595 A | 10/1963 | Overment |
| 3,397,699 A | 8/1968 | Kohl |
| 3,426,364 A | 2/1969 | Lumb |
| 3,486,505 A | 12/1969 | Morrison |
| 3,604,487 A | 9/1971 | Gilbert |

(Continued)

FOREIGN PATENT DOCUMENTS

DE    2821678 A1    11/1979

(Continued)

OTHER PUBLICATIONS

Anasetti et al., "Spine Stability After Implantation of an Interspinous Device: An In Vitro and Finite Element Biomechanical Study," J. Neurosurg. Spine, Nov. 2010, vol. 13, pp. 568-575.

(Continued)

*Primary Examiner* — Eduardo C Robert
*Assistant Examiner* — Jan Christopher Merene

(57) ABSTRACT

Medical devices and related methods for the treatment of spinal conditions are described herein. In one embodiment, an apparatus includes a support member configured to be implanted at least partially in a space between adjacent spinous processes and an actuator coupled to the support member. The apparatus also includes an elongate retention member having a first end coupled to the actuator and a second end coupled to either the support member or the actuator. The actuator is configured to be rotated such that the first end moves from a first location at a first distance from the second end, to a second location at a second distance from the second end. At least a portion of the elongate retention member is disposed at a non-zero distance from an outer surface of the support member when the first end of the elongate retention member is at its second location.

12 Claims, 10 Drawing Sheets

U.S. PATENT DOCUMENTS

| | | |
|---|---|---|
| 3,648,691 A | 3/1972 | Lumb et al. |
| 3,779,239 A | 12/1973 | Fischer et al. |
| 4,011,602 A | 3/1977 | Rybicki et al. |
| 4,237,875 A | 12/1980 | Termanini |
| 4,257,409 A | 3/1981 | Bacal et al. |
| 4,274,324 A | 6/1981 | Giannuzzi |
| 4,289,123 A | 9/1981 | Dunn |
| 4,327,736 A | 5/1982 | Inoue |
| 4,401,112 A | 8/1983 | Rezaian |
| 4,499,636 A | 2/1985 | Tanaka |
| 4,509,517 A | 4/1985 | Zibelin |
| 4,519,100 A | 5/1985 | Wills et al. |
| 4,553,273 A | 11/1985 | Wu |
| 4,554,914 A | 11/1985 | Kapp et al. |
| 4,557,259 A | 12/1985 | Wu |
| 4,573,454 A | 3/1986 | Hoffman |
| 4,592,341 A | 6/1986 | Omagari et al. |
| 4,599,086 A | 7/1986 | Doty |
| 4,604,995 A | 8/1986 | Stephens et al. |
| 4,611,582 A | 9/1986 | Duff |
| 4,632,101 A | 12/1986 | Freedland |
| 4,636,217 A | 1/1987 | Ogilvie et al. |
| 4,646,998 A | 3/1987 | Pate |
| 4,657,550 A | 4/1987 | Daher |
| 4,662,808 A | 5/1987 | Camilleri |
| 4,686,970 A | 8/1987 | Dove et al. |
| 4,704,057 A | 11/1987 | McSherry |
| 4,721,103 A | 1/1988 | Freedland |
| 4,759,769 A | 7/1988 | Hedman et al. |
| 4,787,378 A | 11/1988 | Sodhi |
| 4,822,226 A | 4/1989 | Kennedy |
| 4,827,918 A | 5/1989 | Olerud |
| 4,834,600 A | 5/1989 | Lemke |
| 4,862,891 A | 9/1989 | Smith |
| 4,863,476 A | 9/1989 | Shepperd |
| 4,886,405 A | 12/1989 | Blomberg |
| 4,892,545 A | 1/1990 | Day et al. |
| 4,913,144 A | 4/1990 | Del Medico |
| 4,931,055 A | 6/1990 | Bumpus et al. |
| 4,932,975 A | 6/1990 | Main et al. |
| 4,969,887 A | 11/1990 | Sodhi |
| 4,997,432 A | 3/1991 | Keller |
| 5,000,166 A | 3/1991 | Karpf |
| 5,011,484 A | 4/1991 | Breard |
| 5,047,055 A | 9/1991 | Bao et al. |
| 5,059,193 A | 10/1991 | Kuslich |
| 5,092,866 A | 3/1992 | Breard et al. |
| 5,097,820 A | 3/1992 | Shulman et al. |
| 5,098,433 A | 3/1992 | Freedland |
| 5,171,278 A | 12/1992 | Pisharodi |
| 5,201,734 A | 4/1993 | Cozad et al. |
| 5,267,999 A | 12/1993 | Olerud |
| 5,290,312 A | 3/1994 | Kojimoto et al. |
| 5,306,275 A | 4/1994 | Bryan |
| 5,306,310 A | 4/1994 | Siebels |
| 5,312,405 A | 5/1994 | Korotko et al. |
| 5,316,422 A | 5/1994 | Coffman |
| 5,356,423 A | 10/1994 | Tihon et al. |
| 5,360,430 A | 11/1994 | Lin |
| 5,366,455 A | 11/1994 | Dove et al. |
| 5,370,697 A | 12/1994 | Baumgartner |
| 5,390,683 A | 2/1995 | Pisharodi |
| 5,395,370 A | 3/1995 | Muller et al. |
| 5,401,269 A | 3/1995 | Buttner-Janz et al. |
| 5,403,316 A | 4/1995 | Ashman |
| 5,415,661 A | 5/1995 | Holmes |
| 5,437,672 A | 8/1995 | Alleyne |
| 5,437,674 A | 8/1995 | Worcel et al. |
| 5,439,463 A | 8/1995 | Lin |
| 5,454,812 A | 10/1995 | Lin |
| 5,456,689 A | 10/1995 | Kresch et al. |
| 5,458,641 A | 10/1995 | Ramirez Jimenez |
| 5,480,442 A | 1/1996 | Bertagnoli |
| 5,484,440 A | 1/1996 | Allard |
| 5,489,307 A | 2/1996 | Kuslich et al. |
| 5,496,318 A | 3/1996 | Howland et al. |
| 5,518,498 A | 5/1996 | Lindenberg et al. |
| 5,536,268 A | 7/1996 | Griss |
| 5,545,170 A | 8/1996 | Hart |
| 5,554,191 A | 9/1996 | Lahille et al. |
| 5,562,662 A | 10/1996 | Brumfield et al. |
| 5,562,735 A | 10/1996 | Margulies |
| 5,571,192 A | 11/1996 | Schonhoffer |
| 5,599,279 A | 2/1997 | Slotman et al. |
| 5,609,634 A | 3/1997 | Voydeville |
| 5,609,635 A | 3/1997 | Michelson |
| 5,609,636 A | 3/1997 | Kohrs et al. |
| 5,628,756 A | 5/1997 | Barker, Jr. et al. |
| 5,630,816 A | 5/1997 | Kambin |
| 5,645,599 A | 7/1997 | Samani |
| 5,653,762 A | 8/1997 | Pisharodi |
| 5,653,763 A | 8/1997 | Errico et al. |
| 5,658,335 A | 8/1997 | Allen |
| 5,662,657 A | 9/1997 | Carn |
| 5,665,096 A | 9/1997 | Yoon |
| 5,665,122 A | 9/1997 | Kambin |
| 5,667,513 A | 9/1997 | Torrie et al. |
| 5,674,295 A | 10/1997 | Ray et al. |
| 5,676,702 A | 10/1997 | Ratron |
| 5,683,464 A | 11/1997 | Wagner et al. |
| 5,685,826 A | 11/1997 | Bonutti |
| 5,690,649 A | 11/1997 | Li |
| 5,693,100 A | 12/1997 | Pisharodi |
| 5,702,395 A | 12/1997 | Hopf |
| 5,702,452 A | 12/1997 | Argenson et al. |
| 5,702,455 A | 12/1997 | Saggar |
| 5,707,390 A | 1/1998 | Bonutti |
| 5,716,416 A | 2/1998 | Lin |
| 5,723,013 A | 3/1998 | Jeanson et al. |
| 5,725,341 A | 3/1998 | Hofmeister |
| 5,746,762 A | 5/1998 | Bass |
| 5,755,797 A | 5/1998 | Baumgartner |
| 5,772,661 A | 6/1998 | Michelson |
| 5,792,085 A | 8/1998 | Walters |
| 5,797,909 A | 8/1998 | Michelson |
| 5,800,547 A | 9/1998 | Schafer et al. |
| 5,800,549 A | 9/1998 | Bao et al. |
| 5,810,815 A | 9/1998 | Morales |
| 5,836,948 A | 11/1998 | Zucherman et al. |
| 5,849,004 A | 12/1998 | Bramlet |
| 5,860,977 A | 1/1999 | Zucherman et al. |
| 5,888,196 A | 3/1999 | Bonutti |
| 5,888,224 A | 3/1999 | Beckers et al. |
| 5,893,890 A | 4/1999 | Pisharodi |
| 5,941,881 A | 8/1999 | Barnes |
| 5,976,186 A | 11/1999 | Bao et al. |
| 5,980,523 A | 11/1999 | Jackson |
| 6,022,376 A | 2/2000 | Assell et al. |
| 6,042,582 A | 3/2000 | Ray |
| 6,048,342 A | 4/2000 | Zucherman et al. |
| 6,059,829 A | 5/2000 | Schlapfer et al. |
| 6,068,630 A | 5/2000 | Zucherman et al. |
| 6,074,390 A | 6/2000 | Zucherman et al. |
| 6,083,225 A | 7/2000 | Winslow et al. |
| 6,086,595 A | 7/2000 | Yonemura et al. |
| 6,102,922 A | 8/2000 | Jakobsson et al. |
| 6,113,602 A | 9/2000 | Sand |
| 6,126,689 A | 10/2000 | Brett |
| 6,126,691 A | 10/2000 | Kasra et al. |
| 6,127,597 A | 10/2000 | Beyar et al. |
| 6,132,464 A | 10/2000 | Martin |
| 6,139,549 A | 10/2000 | Keller |
| 6,159,212 A | 12/2000 | Schoedinger, III et al. |
| 6,171,339 B1 | 1/2001 | Houfburg et al. |
| 6,174,311 B1 | 1/2001 | Branch et al. |
| 6,190,413 B1 | 2/2001 | Sutcliffe |
| 6,190,414 B1 | 2/2001 | Young |
| 6,214,037 B1 | 4/2001 | Mitchell et al. |
| 6,214,050 B1 | 4/2001 | Huene |
| 6,224,607 B1 | 5/2001 | Michelson |
| 6,224,631 B1 | 5/2001 | Kohrs |
| 6,241,729 B1 | 6/2001 | Estes et al. |
| 6,245,107 B1 | 6/2001 | Ferree |
| 6,261,296 B1 | 7/2001 | Aebi et al. |
| 6,261,586 B1 | 7/2001 | McKay |
| 6,293,949 B1 | 9/2001 | Justis et al. |
| 6,336,930 B1 | 1/2002 | Stalcup et al. |

| Patent/Pub No. | Date | Name |
|---|---|---|
| 6,348,053 B1 | 2/2002 | Cachia |
| 6,352,537 B1 | 3/2002 | Strnad |
| 6,364,883 B1 | 4/2002 | Santilli |
| 6,371,987 B1 | 4/2002 | Weiland et al. |
| 6,375,682 B1 | 4/2002 | Fleischmann et al. |
| 6,402,750 B1 | 6/2002 | Atkinson et al. |
| 6,402,751 B1 | 6/2002 | Hoeck et al. |
| 6,419,703 B1 | 7/2002 | Fallin et al. |
| 6,419,704 B1 | 7/2002 | Ferree |
| 6,432,130 B1 | 8/2002 | Hanson |
| 6,440,169 B1 | 8/2002 | Elberg et al. |
| 6,447,513 B1 | 9/2002 | Griggs |
| 6,451,019 B1 | 9/2002 | Zucherman et al. |
| 6,500,178 B2 | 12/2002 | Zucherman et al. |
| 6,511,508 B1 | 1/2003 | Shahinpoor et al. |
| 6,514,256 B2 | 2/2003 | Zucherman et al. |
| 6,520,991 B2 | 2/2003 | Huene |
| 6,554,833 B2 | 4/2003 | Levy |
| 6,565,570 B2 | 5/2003 | Sterett et al. |
| 6,582,433 B2 | 6/2003 | Yun |
| 6,582,467 B1 | 6/2003 | Teitelbaum et al. |
| 6,592,585 B2 | 7/2003 | Lee et al. |
| 6,602,260 B2 | 8/2003 | Harari et al. |
| 6,610,065 B1 | 8/2003 | Branch et al. |
| 6,626,944 B1 | 9/2003 | Taylor |
| 6,645,207 B2 | 11/2003 | Dixon et al. |
| 6,652,533 B2 | 11/2003 | O'Neil |
| 6,669,729 B2 | 12/2003 | Chin |
| 6,676,665 B2 | 1/2004 | Foley et al. |
| 6,685,742 B1 | 2/2004 | Jackson |
| 6,695,842 B2 | 2/2004 | Zucherman et al. |
| 6,699,246 B2 | 3/2004 | Zucherman et al. |
| 6,709,435 B2 | 3/2004 | Lin |
| 6,712,819 B2 | 3/2004 | Zucherman et al. |
| 6,723,126 B1 | 4/2004 | Berry |
| 6,730,126 B2 | 5/2004 | Boehm, Jr. et al. |
| 6,733,531 B1 | 5/2004 | Trieu |
| 6,733,534 B2 | 5/2004 | Sherman |
| 6,736,818 B2 | 5/2004 | Perren et al. |
| 6,743,257 B2 | 6/2004 | Castro |
| 6,752,832 B2 | 6/2004 | Neumann |
| 6,758,863 B2 | 7/2004 | Estes et al. |
| 6,761,720 B1 | 7/2004 | Senegas |
| 6,770,096 B2 | 8/2004 | Bolger et al. |
| 6,783,530 B1 | 8/2004 | Levy |
| 6,835,205 B2 | 12/2004 | Atkinson et al. |
| 6,857,343 B1 | 2/2005 | Easterbrooks et al. |
| 6,902,580 B2 | 6/2005 | Fallin et al. |
| 6,905,512 B2 | 6/2005 | Paes et al. |
| 6,946,000 B2 | 9/2005 | Senegas et al. |
| 6,981,975 B2 | 1/2006 | Michelson |
| 7,011,685 B2 | 3/2006 | Arnin et al. |
| 7,041,136 B2 | 5/2006 | Goble et al. |
| 7,048,736 B2 | 5/2006 | Robinson et al. |
| 7,070,598 B2 | 7/2006 | Lim et al. |
| 7,081,120 B2 | 7/2006 | Li et al. |
| 7,087,055 B2 | 8/2006 | Lim et al. |
| 7,087,083 B2 | 8/2006 | Pasquet et al. |
| 7,097,648 B1 | 8/2006 | Globerman et al. |
| 7,097,654 B1 | 8/2006 | Freedland |
| 7,101,375 B2 | 9/2006 | Zucherman et al. |
| 7,163,558 B2 | 1/2007 | Senegas et al. |
| 7,189,234 B2 | 3/2007 | Zucherman et al. |
| 7,201,751 B2 | 4/2007 | Zucherman et al. |
| 7,217,293 B2 | 5/2007 | Branch, Jr. |
| 7,238,204 B2 | 7/2007 | Le Couedic et al. |
| 7,252,673 B2 | 8/2007 | Lim |
| 7,306,628 B2 | 12/2007 | Zucherman et al. |
| 7,335,203 B2 | 2/2008 | Winslow et al. |
| 7,377,942 B2 | 5/2008 | Berry |
| 7,431,735 B2 | 10/2008 | Liu et al. |
| 7,442,208 B2 | 10/2008 | Mathieu et al. |
| 7,445,637 B2 | 11/2008 | Taylor |
| 7,458,981 B2 | 12/2008 | Fielding et al. |
| 7,524,324 B2 | 4/2009 | Winslow et al. |
| 7,582,106 B2 | 9/2009 | Teitelbaum et al. |
| 7,604,652 B2 | 10/2009 | Arnin et al. |
| 7,611,316 B2 | 11/2009 | Panasik et al. |
| 7,621,950 B1 | 11/2009 | Globerman et al. |
| 7,658,752 B2 | 2/2010 | Labrom et al. |
| 7,749,252 B2 | 7/2010 | Zucherman et al. |
| 7,771,456 B2 | 8/2010 | Hartmann et al. |
| 7,862,615 B2 | 1/2011 | Carli et al. |
| 7,901,430 B2 | 3/2011 | Matsuura et al. |
| 2001/0016743 A1 | 8/2001 | Zucherman et al. |
| 2002/0082600 A1 | 6/2002 | Shaolian et al. |
| 2002/0143331 A1 | 10/2002 | Zucherman et al. |
| 2002/0161368 A1 | 10/2002 | Foley et al. |
| 2003/0040746 A1 | 2/2003 | Mitchell et al. |
| 2003/0045940 A1 | 3/2003 | Eberlein et al. |
| 2003/0065330 A1 | 4/2003 | Zucherman et al. |
| 2003/0120328 A1 | 6/2003 | Jenkins et al. |
| 2003/0153915 A1 | 8/2003 | Nekozuka et al. |
| 2004/0010312 A1 | 1/2004 | Enayati |
| 2004/0010316 A1 | 1/2004 | William et al. |
| 2004/0059318 A1 | 3/2004 | Zhang et al. |
| 2004/0087947 A1 | 5/2004 | Lim et al. |
| 2004/0097931 A1 | 5/2004 | Mitchell |
| 2004/0106927 A1 | 6/2004 | Ruffner et al. |
| 2004/0106995 A1 | 6/2004 | LeCouedic et al. |
| 2004/0117017 A1 | 6/2004 | Pasquet et al. |
| 2004/0133204 A1 | 7/2004 | Davies |
| 2004/0133280 A1 | 7/2004 | Trieu |
| 2004/0138662 A1 | 7/2004 | Landry et al. |
| 2004/0158248 A1 | 8/2004 | Ginn |
| 2004/0167625 A1 | 8/2004 | Beyar et al. |
| 2004/0199255 A1 | 10/2004 | Mathieu et al. |
| 2004/0249388 A1 | 12/2004 | Michelson |
| 2004/0260397 A1 | 12/2004 | Lambrecht et al. |
| 2005/0010293 A1 | 1/2005 | Zucherman et al. |
| 2005/0033434 A1 | 2/2005 | Berry |
| 2005/0049590 A1* | 3/2005 | Alleyne et al. .................. 606/61 |
| 2005/0049708 A1 | 3/2005 | Atkinson et al. |
| 2005/0085814 A1 | 4/2005 | Sherman et al. |
| 2005/0090824 A1 | 4/2005 | Shluzas et al. |
| 2005/0113832 A1 | 5/2005 | Molz, IV et al. |
| 2005/0113842 A1 | 5/2005 | Bertagnoli et al. |
| 2005/0119665 A1 | 6/2005 | Keller |
| 2005/0143827 A1 | 6/2005 | Globerman et al. |
| 2005/0149035 A1 | 7/2005 | Pimenta et al. |
| 2005/0165398 A1 | 7/2005 | Reiley |
| 2005/0203512 A1 | 9/2005 | Hawkins et al. |
| 2005/0203519 A1 | 9/2005 | Harms et al. |
| 2005/0203624 A1 | 9/2005 | Serhan et al. |
| 2005/0216002 A1 | 9/2005 | Simonson |
| 2005/0228391 A1 | 10/2005 | Levy et al. |
| 2005/0245937 A1 | 11/2005 | Winslow |
| 2005/0261768 A1 | 11/2005 | Trieu |
| 2005/0267579 A1 | 12/2005 | Reiley et al. |
| 2005/0273166 A1 | 12/2005 | Sweeney |
| 2005/0277934 A1 | 12/2005 | Vardiman |
| 2005/0288672 A1 | 12/2005 | Ferree |
| 2006/0004447 A1 | 1/2006 | Mastrorio et al. |
| 2006/0004455 A1 | 1/2006 | Leonard et al. |
| 2006/0015181 A1 | 1/2006 | Elberg |
| 2006/0036254 A1 | 2/2006 | Lim |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0085069 A1 | 4/2006 | Kim |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0095136 A1 | 5/2006 | McLuen |
| 2006/0106381 A1 | 5/2006 | Ferree et al. |
| 2006/0106397 A1 | 5/2006 | Lins |
| 2006/0111728 A1 | 5/2006 | Abdou |
| 2006/0116690 A1 | 6/2006 | Pagano |
| 2006/0122620 A1 | 6/2006 | Kim |
| 2006/0129239 A1 | 6/2006 | Kwak |
| 2006/0136060 A1 | 6/2006 | Taylor |
| 2006/0142858 A1 | 6/2006 | Colleran et al. |
| 2006/0149242 A1 | 7/2006 | Kraus et al. |
| 2006/0182515 A1 | 8/2006 | Panasik et al. |
| 2006/0184247 A1 | 8/2006 | Edidin et al. |

| | | |
|---|---|---|
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0224159 A1 | 10/2006 | Anderson |
| 2006/0224241 A1 | 10/2006 | Butler et al. |
| 2006/0235387 A1 | 10/2006 | Peterman |
| 2006/0235426 A1 | 10/2006 | Lim et al. |
| 2006/0235532 A1 | 10/2006 | Meunier et al. |
| 2006/0241601 A1 | 10/2006 | Trautwein et al. |
| 2006/0241613 A1 | 10/2006 | Bruneau et al. |
| 2006/0241643 A1 | 10/2006 | Lim et al. |
| 2006/0241757 A1 | 10/2006 | Anderson |
| 2006/0247623 A1 | 11/2006 | Anderson et al. |
| 2006/0247640 A1 | 11/2006 | Blackwell et al. |
| 2006/0264938 A1 | 11/2006 | Zucherman et al. |
| 2006/0271044 A1 | 11/2006 | Petrini et al. |
| 2006/0271049 A1 | 11/2006 | Zucherman et al. |
| 2006/0271061 A1 | 11/2006 | Beyar et al. |
| 2006/0282075 A1 | 12/2006 | Labrom et al. |
| 2006/0282079 A1 | 12/2006 | Labrom et al. |
| 2006/0293662 A1 | 12/2006 | Boyer et al. |
| 2006/0293663 A1 | 12/2006 | Walkenhorst et al. |
| 2007/0005064 A1 | 1/2007 | Anderson et al. |
| 2007/0010813 A1 | 1/2007 | Zucherman et al. |
| 2007/0032790 A1 | 2/2007 | Aschmann et al. |
| 2007/0043362 A1 | 2/2007 | Malandain et al. |
| 2007/0043363 A1 | 2/2007 | Malandain et al. |
| 2007/0049935 A1* | 3/2007 | Edidin et al. ............... 606/61 |
| 2007/0073289 A1 | 3/2007 | Kwak et al. |
| 2007/0100340 A1 | 5/2007 | Lange et al. |
| 2007/0112354 A1 | 5/2007 | Iwasaki et al. |
| 2007/0123861 A1 | 5/2007 | Dewey et al. |
| 2007/0142915 A1 | 6/2007 | Altarac et al. |
| 2007/0151116 A1 | 7/2007 | Malandain |
| 2007/0162000 A1 | 7/2007 | Perkins |
| 2007/0167945 A1 | 7/2007 | Lange et al. |
| 2007/0173822 A1 | 7/2007 | Bruneau et al. |
| 2007/0173823 A1 | 7/2007 | Dewey et al. |
| 2007/0191833 A1 | 8/2007 | Bruneau et al. |
| 2007/0191834 A1 | 8/2007 | Bruneau et al. |
| 2007/0191837 A1 | 8/2007 | Trieu |
| 2007/0191838 A1 | 8/2007 | Bruneau et al. |
| 2007/0198091 A1 | 8/2007 | Boyer et al. |
| 2007/0225706 A1* | 9/2007 | Clark et al. ............... 606/61 |
| 2007/0225807 A1 | 9/2007 | Phan et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233081 A1 | 10/2007 | Pasquet et al. |
| 2007/0233089 A1 | 10/2007 | DiPoto et al. |
| 2007/0250060 A1 | 10/2007 | Anderson et al. |
| 2007/0270823 A1 | 11/2007 | Trieu et al. |
| 2007/0270824 A1 | 11/2007 | Lim et al. |
| 2007/0270825 A1 | 11/2007 | Carls et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0270874 A1 | 11/2007 | Anderson |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276493 A1 | 11/2007 | Malandain et al. |
| 2007/0276496 A1 | 11/2007 | Lange et al. |
| 2007/0276497 A1 | 11/2007 | Anderson |
| 2007/0282443 A1 | 12/2007 | Globerman et al. |
| 2008/0021457 A1 | 1/2008 | Anderson et al. |
| 2008/0021460 A1 | 1/2008 | Bruneau et al. |
| 2008/0058934 A1 | 3/2008 | Malandain et al. |
| 2008/0097446 A1 | 4/2008 | Reiley et al. |
| 2008/0108990 A1* | 5/2008 | Mitchell et al. ............... 606/61 |
| 2008/0114357 A1 | 5/2008 | Allard et al. |
| 2008/0114358 A1 | 5/2008 | Anderson et al. |
| 2008/0114456 A1 | 5/2008 | Dewey et al. |
| 2008/0147190 A1 | 6/2008 | Dewey et al. |
| 2008/0161818 A1 | 7/2008 | Kloss et al. |
| 2008/0167685 A1 | 7/2008 | Allard et al. |
| 2008/0177306 A1* | 7/2008 | Lamborne et al. ............... 606/246 |
| 2008/0183209 A1 | 7/2008 | Robinson et al. |
| 2008/0183211 A1 | 7/2008 | Lamborne et al. |
| 2008/0183218 A1 | 7/2008 | Mueller et al. |
| 2008/0195152 A1 | 8/2008 | Altarac et al. |
| 2008/0215094 A1 | 9/2008 | Taylor |
| 2008/0221685 A9 | 9/2008 | Altarac et al. |
| 2008/0234824 A1 | 9/2008 | Youssef et al. |
| 2008/0262617 A1 | 10/2008 | Froehlich et al. |
| 2008/0281360 A1 | 11/2008 | Vittur et al. |
| 2008/0281361 A1 | 11/2008 | Vittur et al. |
| 2009/0062915 A1 | 3/2009 | Kohm et al. |
| 2009/0105766 A1 | 4/2009 | Thompson et al. |
| 2009/0105773 A1 | 4/2009 | Lange et al. |
| 2009/0234389 A1 | 9/2009 | Chuang et al. |
| 2009/0240283 A1 | 9/2009 | Carls et al. |
| 2009/0270918 A1 | 10/2009 | Attia et al. |
| 2009/0326581 A1* | 12/2009 | Galley et al. ............... 606/249 |
| 2010/0121379 A1 | 5/2010 | Edmond |
| 2010/0204732 A1 | 8/2010 | Aschmann et al. |

FOREIGN PATENT DOCUMENTS

| | | |
|---|---|---|
| DE | 3922044 A1 | 2/1991 |
| DE | 4012622 C1 | 7/1991 |
| DE | 4217660 A1 | 12/1993 |
| EP | 0322334 B1 | 2/1992 |
| EP | 0767636 B1 | 1/1999 |
| EP | 1004276 A1 | 5/2000 |
| EP | 1011464 B1 | 6/2000 |
| EP | 1138268 A1 | 10/2001 |
| EP | 1148850 B1 | 10/2001 |
| EP | 1148851 B1 | 10/2001 |
| EP | 1302169 A1 | 4/2003 |
| EP | 1330987 A1 | 7/2003 |
| EP | 1152797 A2 | 7/2005 |
| EP | 1854433 A1 | 11/2007 |
| EP | 1905392 A1 | 4/2008 |
| EP | 1982664 A1 | 10/2008 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2731643 A1 | 9/1996 |
| FR | 2775183 A1 | 8/1999 |
| FR | 2799948 A1 | 4/2001 |
| FR | 2816197 A1 | 5/2002 |
| JP | 02-224660 | 9/1990 |
| JP | 09-075381 | 3/1997 |
| JP | 2003079649 | 3/2003 |
| SU | 988281 | 1/1983 |
| SU | 1484348 A1 | 6/1989 |
| WO | WO 94/26192 | 11/1994 |
| WO | WO 94/26195 | 11/1994 |
| WO | WO 97/18769 | 5/1997 |
| WO | WO 98/20939 | 5/1998 |
| WO | WO 99/26562 | 6/1999 |
| WO | WO 00/44319 | 8/2000 |
| WO | WO 01/54598 A1 | 8/2001 |
| WO | WO 03/057055 A1 | 7/2003 |
| WO | WO 2004/047689 A1 | 6/2004 |
| WO | WO 2004/047691 A1 | 6/2004 |
| WO | WO 2004/084743 A1 | 10/2004 |
| WO | WO 2004/084768 A2 | 10/2004 |
| WO | WO 2004/110300 A2 | 12/2004 |
| WO | WO 2005/009300 A1 | 2/2005 |
| WO | WO 2005/011507 A1 | 2/2005 |
| WO | WO 2005/044118 A1 | 5/2005 |
| WO | WO 2005/048856 A1 | 6/2005 |
| WO | WO 2005/110258 A1 | 11/2005 |
| WO | WO 2006/064356 A1 | 6/2006 |
| WO | WO 2007/034516 A1 | 3/2007 |
| WO | WO 2007052975 A1 | 5/2007 |

| WO | WO 2009/083276 A1 | 7/2009 |
| WO | WO 2009/083583 A1 | 7/2009 |
| WO | WO 2009/098536 A1 | 8/2009 |

OTHER PUBLICATIONS

Bellini et al., "Biomechanics of the Lumbar Spine Afer Dynamic Stabilization," J. Spinal Discord Tech., 2006, vol. 00, No. 00, pp. 1-7.
Buric et al., "DIAM Device for Low Back Pain in Degenerative Disc Disease 24 Months Follow-up," Advances in Minimally Invasive Surgery and Therapy for Spine and Nerves, Alexandre et al., eds., 2011, pp. 177-182, Spinger-Verlat/Wien.
Kramer et al., "Intervetertebral Disk Diseases: Causes, Diagnosis, Treatment and Prophylaxis," pp. 244-249, Medical, 1990.
Phillips et al., "Biomechanics of Posterior Dynamic Stabiling Device (DIAM) After Facetectomy and Disectomy," The Spine Journal, 2006, vol. 6, pp. 714-722.
Taylor et al., "Device for Intervertebral Assisted Motion: Technique and Intial Results," 22 Neurosurg. Focus, Jan. 2007, vol. 22, No. 1, pp. 1-6.
Wilke et al., "Biomedical Effect of Different Lumbar Interspinous Implants on Flexibilty and Intradiscal Pressure," Eur Spine J., Vo. 17, published online Jun. 27, 2008, pp. 1049-1056.
Zdeblick et al., "Two-Point Fixation of the Lumbar Spine Differential Stability in Rotation," SPINE, 1991, pp. S298-S301, vol. 16, No. 6, Supplement.
Zhao et al., "Efficacy of the Dynamic Interspinous Assisted Motion System in Clinical Treatment of Degenerative Lumbar Disease," Chin. Med. J., 2010, vol. 123, No. 21, pp. 2974-2977.
"Dispositivo Intervertebrale Ammortizzante DIAM," date unknown, p. 1.
"Tecnica Operatoria Per Il Posizionamento Della Protesi DIAM," date unknown, pp. 1-3.
"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.
Benzel et al., "Posterior Cervical Interspinous Compression Wiring and Fusion for Mid to Low Cervical Spinal Injuries," J. Neurosurg., Jun. 1989, pp. 893-899, vol. 70.
Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.
Christie et al., "Dynamic Interspinous Process Technology," SPINE, 2005, pp. S73-S78, vol. 30, No. 16S.
Cousin Biotech, "Analysis of Clinical Experience with a Posterior Shock-Absorbing Implant," date unknown, pp. 2-9.
Cousin Biotech, Dispositif Intervertébral Amortissant, Jun. 1998, pp. 1-4.
Cousin Biotech, Technique Operatoire de la Prothese DIAM, date unknown, Annexe 1, pp. 1-8.
Dickman et al., "The Interspinous Method of Posterior Atlantoaxial Arthrodesis," J. Neurosurg., Feb. 1991, pp. 190-198, vol. 74.
Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.
Ebara et al., "Inoperative Measurement of Lumbar Spinal Instability," SPINE, 1992, pp. S44-S50, vol. 17, No. 3S.
Fassio et al., "Treatment of Degenerative Lumbar Spinal Instability L4-L5 by Interspinous Ligamentoplasty," Rachis, Dec. 1991, pp. 465-474, vol. 3, No. 6.
Fassio, "Mise au Point Sur la Ligamentoplastie Inter-Epineuse Lombaire Dans les Instabilites," Maîtrise Orthopédique, Jul. 1993, pp. 18, No. 25.
Garner et al., "Development and Preclinical Testing of a New Tension-Band Device for the Spine: the Loop System," Eur. Spine J., Aug. 7, 2002, pp. S186-S191, vol. 11, Suppl. 2.
Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.
Hambly et al., "Tension Band Wiring-Bone Grafting for Spondylolysis and Spondylolisthesis," SPINE, 1989, pp. 455-460, vol. 14, No. 4.
Kiwerski, "Rehabilitation of Patients with Thoracic Spine Injury Treated by Spring Alloplasty," Int. J. Rehab. Research, 1983, pp. 469-474, vol. 6, No. 4.
Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.
Mah et al., "Threaded K-Wire Spinous Process Fixation of the Axis for Modified Gallie Fusion in Children and Adolescents," J. Pediatric Othopaedics, 1989, pp. 675-679, vol. 9.
Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.
McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.
Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.
Müller, "Restauration Dynamique de la Stabilité Rachidienne," Tiré de la Sulzer Technical Review, Jan. 1999, Sulzer Management Ltd, Winterthur, Switzerland.
Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.
Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90° Congresso, Jun. 21-23, 2001, Paestum.
Petrini et al., "Stabilizzazione Elastica," Patologia Degenerativa del Rachide Lombare, Oct. 5-6, 2001, Rimini.
Porter, "Spinal Stenosis and Neurogenic Claudication," SPINE, Sep. 1, 1996, pp. 2046-2052, vol. 21, No. 17.
Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.
Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.
Richards et al., "The Treatment Mechanism of an Interspinous Process Implant for Lumbar Neurogenic Intermittent Claudication," SPINE, 2005, pp. 744-749, vol. 30, No. 7.
Scarfó, "Instability/Stenosis: Holistic Approach for Less Invasive Surgery," date unknown, University of Siena, Siena, Italy.
Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.
Schlegel et al., "The Role of Distraction in Improving the Space Available in the Lumbar Stenotic Canal and Foramen," SPINE, 1994, pp. 2041-2047, vol. 19, No. 18.
Senegas et al., "Le Recalibrage du Canal Lombaire, Alternative á la Laminectomie dans le Traitement des Sténoses du Canal Lombaire," Revue de Chirurgie Orthopédique, 1988, pp. 15-22.
Senegas et al., "Stabilisation Lombaire Souple," Instabilité Vertébrales Lombaires, Gastambide, ed., 1995, pp. 122-132, Expansion Scientifique Française, Paris, France.
Senegas, "La Ligamentoplastie Inter Vertébrale Lombaire, Alternative a L'Arthrodèse," La Revue de Medécine Orthopédique, Jun. 1990, pp. 33-35, No. 20.
Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," Spine, Jul. 1992, pp. 834-837, vol. 17, No. 7.

* cited by examiner

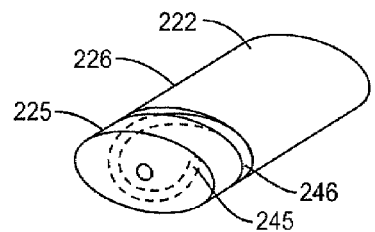
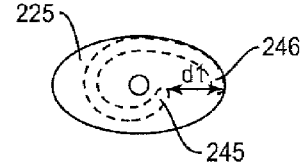
FIG. 12  FIG. 13
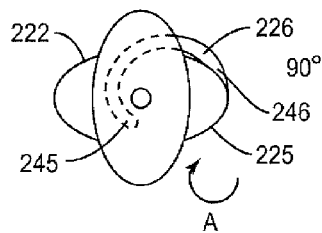
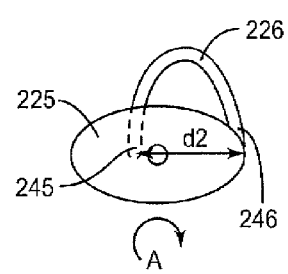
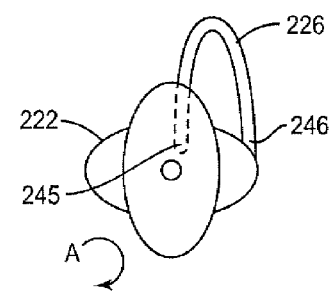
FIG. 14  FIG. 15  FIG. 16
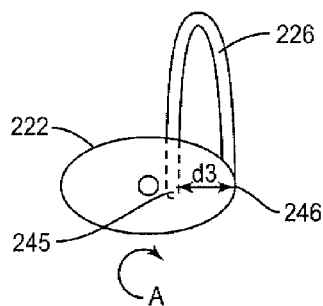
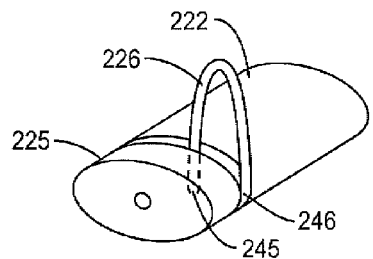
FIG. 17  FIG. 18

EXTENSION LIMITING DEVICES AND METHODS OF USE FOR THE SPINE

BACKGROUND

The invention relates generally to the treatment of spinal conditions, and more particularly, to the treatment of spinal compression using percutaneous spinal implants for implantation between adjacent spinous processes.

A back condition that impacts many individuals is spinal stenosis. Spinal stenosis is a progressive narrowing of the spinal canal that causes compression of the spinal cord. Each vertebra in the spinal column has an opening that extends through it. The openings are aligned vertically to form the spinal canal. The spinal cord runs through the spinal canal. As the spinal canal narrows, the spinal cord and nerve roots extending from the spinal cord and between adjacent vertebrae are compressed and may become inflamed. Spinal stenosis can cause pain, weakness, numbness, burning sensations, tingling, and in particularly severe cases, may cause loss of bladder or bowel function, or paralysis. The legs, calves and buttocks are most commonly affected by spinal stenosis, however, the shoulders and arms may also be affected.

Mild cases of spinal stenosis may be treated with rest or restricted activity, non-steroidal anti-inflammatory drugs (e.g., aspirin), corticosteroid injections (epidural steroids), and/or physical therapy. Some patients find that bending forward, sitting or lying down may help relieve the pain. This may be due to bending forward resulting in more vertebral space (i.e., space between adjacent vertebrae), which may temporarily relieve nerve compression. Because spinal stenosis is a progressive disease, the source of pressure may have to be surgically corrected (decompressive laminectomy) as the patient has increasing pain. The surgical procedure can remove bone and other tissues that have impinged upon the spinal canal or put pressure on the spinal cord. Two adjacent vertebrae may also be fused during the surgical procedure to prevent an area of instability, improper alignment or slippage, such as that caused by spondylolisthesis. Surgical decompression can relieve pressure on the spinal cord or spinal nerve by widening the spinal canal. This procedure requires that the patient be given a general anesthesia as an incision is made in the patient to access the spine to remove the areas that are contributing to the pressure. This procedure, however, may result in blood loss and an increased chance of significant complications, and usually results in an extended hospital stay.

Thus, a need exists for improvements in the treatment of spinal conditions such as spinal stenosis.

SUMMARY OF THE INVENTION

Medical devices and related methods for the treatment of spinal conditions are described herein. In one embodiment, an apparatus includes a support member that defines a longitudinal axis and that is configured to be implanted at least partially into a space between adjacent spinous processes and an actuator coupled to the support member. The apparatus also includes an elongate retention member having a first end and a second end. The first end is coupled to the actuator and the second end is coupled to either the support member or the actuator. The actuator is configured to be rotated relative to the support member such that the second end maintains a longitudinal position and the first end of the elongate retention member moves from a first location in which the first end of the elongate retention member is at a first distance from the second end of the elongate retention member to a second location in which the first end of the elongate retention member is at a second distance from the second end of the elongate retention member. At least a portion of the elongate retention member is disposed at a non-zero distance from an outer surface of the support member when the first end of the elongate retention member is at its second location.

BRIEF DESCRIPTION OF THE DRAWINGS

FIG. 12 is a side perspective view of a proximal end portion of the medical device FIG. 8 shown in the first configuration.

FIG. 13 is an end view of the medical device of FIG. 8 shown in the first configuration.

FIG. 14 is a proximal end view of the medical device of FIG. 8 with the actuator shown rotated 90 degrees relative to the support member.

FIG. 15 is a proximal end view of the medical device of FIG. 8 with the actuator shown rotated 180 degrees relative to the support member.

FIG. 16 is a proximal end view of the medical device of FIG. 8 with the actuator shown rotated 270 degrees relative to the support member.

FIG. 17 is a proximal end view of the medical device of FIG. 8 with the actuator shown rotated 360 degrees relative to the support member.

FIG. 18 is a side perspective view of the proximal end portion of the medical device of FIG. 8 shown in the second configuration.

DETAILED DESCRIPTION

Figure 2:
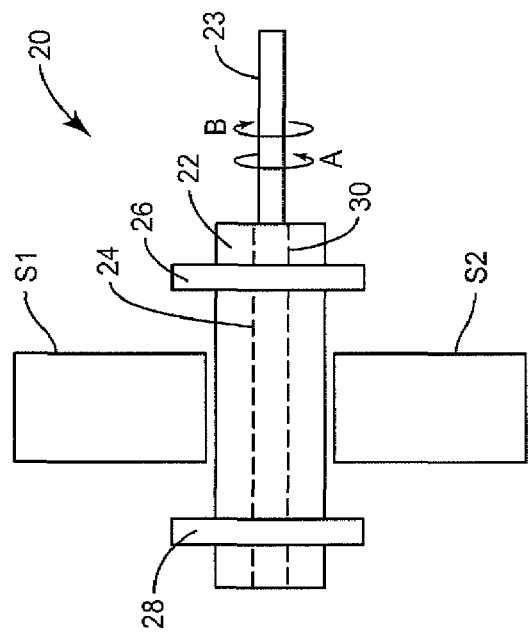
FIG. 2 is a schematic illustration of a posterior view of a medical device according to an embodiment and shown in a second configuration adjacent two adjacent spinous processes.

The devices described herein are configured for deployment within an interior area of a patient's body, such as in a space between adjacent spinous processes. For example, one or more of the devices can be percutaneously inserted within a patient, and can be used to limit extension of adjacent spinous processes. The devices can also be configured to limit lateral movement of the device relative to, for example, the adjacent spinous processes. For example, some devices can be moved between a collapsed or undeployed configuration, and an expanded or deployed configuration. Such devices can be inserted into a patient's body in the collapsed configuration and then moved to the expanded configuration while disposed within the patient's body (e.g., in a space between adjacent spinous processes). In the expanded configuration, expanded portions of the devices can be used to limit lateral movement of the device.

In some embodiments, an apparatus includes a support member that defines a longitudinal axis and that is configured to be implanted at least partially into a space between adjacent spinous processes. The apparatus also includes an actuator coupled to the support member and an elongate retention member having a first end and a second end. The first end of the elongate retention member is coupled to the actuator and the second end of the elongate retention member is coupled to either the support member or the actuator. The actuator is configured to be rotated relative to the support member such that the second end of the elongate retention member maintains a longitudinal position and the first end of the elongate retention member moves from a first location in which the first end of the elongate retention member is at a first distance from the second end of the elongate retention member to a second location in which the first end of the elongate retention member is at a second distance from the second end of the elongate retention member. At least a portion of the elongate retention member is disposed at a non-zero distance from an outer surface of the support member when the first end of the elongate retention member is at its second location.

In some embodiments, a method includes disposing at least a portion of an implant in a space between adjacent spinous processes. The implant has a support member, an actuator coupled to the support member, and an elongate retention member having a first end and a second end. The second end of the elongate retention member is fixed to one of the support member or the actuator. The actuator is rotated in a first direction relative to the support member such that the first end of the elongate retention member moves relative to the second end of the elongate retention member and the elongate retention member is moved to an expanded configuration.

In some embodiments, an apparatus includes a support member configured to be disposed at least partially in a space between adjacent spinous processes and an actuator assembly that includes a first portion, a second portion and an elongate member. The elongate member is moveably disposed at least partially within an interior region defined by the support member. The second portion is disposed at a non-zero distance from the first portion. The elongate member is configured to be rotated relative to the support member such that the first portion moves substantially parallel to a centerline of the support member in a first direction, and the second portion moves substantially parallel to the centerline of the support member in a second direction opposite the first direction, and a retention portion of the apparatus is moved to an expanded configuration.

As used in this specification and the appended claims, the singular forms "a," "an" and "the" include plural referents unless the context clearly dictates otherwise. Thus, for example, the term "a member" is intended to mean a single member or a combination of members, "a material" is intended to mean one or more materials, or a combination thereof. Furthermore, the words "proximal" and "distal" refer to direction closer to and away from, respectively, an operator (e.g., surgeon, physician, nurse, technician, etc.) who would insert the medical device into the patient, with the tip-end (i.e., distal end) of the device inserted inside a patient's body first. Thus, for example, the implant end first inserted inside the patient's body would be the distal end of the implant, while the implant end to last enter the patient's body would be the proximal end of the implant.

The term "body" is used here to mean a mammalian body. For example, a body can be a patient's body, or a cadaver, or a portion of a patient's body or a portion of a cadaver.

The term "parallel" is used herein to describe a relationship between two geometric constructions (e.g., two lines, two planes, a line and a plane, two curved surfaces, a line and a curved surface or the like) in which the two geometric constructions are substantially non-intersecting as they extend substantially to infinity. For example, as used herein, a line is said to be parallel to a curved surface when the line and the curved surface do not intersect as they extend to infinity. Similarly, when a planar surface (i.e., a two-dimensional surface) is said to be parallel to a line, every point along the line is spaced apart from the nearest portion of the surface by a substantially equal distance. Two geometric constructions are described herein as being "parallel" or "substantially parallel" to each other when they are nominally parallel to each other, such as for example, when they are parallel to each other within a tolerance. Such tolerances can include, for example, manufacturing tolerances, measurement tolerances or the like.

Figure 1:
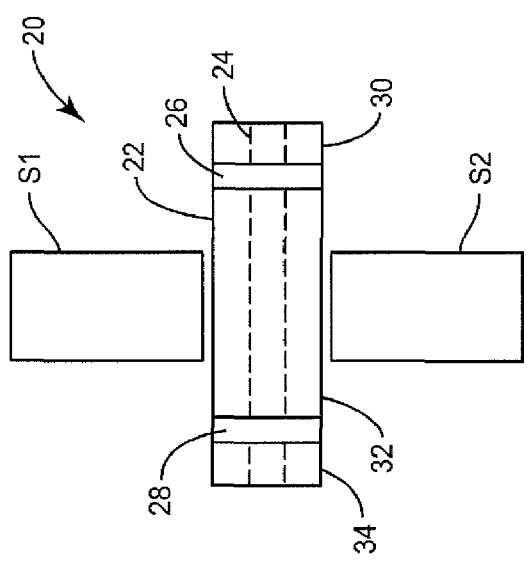
FIG. 1 is a schematic illustration of a posterior view of a medical device according to an embodiment and shown in a first configuration adjacent two adjacent spinous processes.

FIGS. 1 and 2 are each a schematic illustration of a medical device that can be inserted between adjacent anatomical structures, such as in a space between adjacent spinous processes S1 and S2 (shown schematically in FIGS. 1 and 2). A medical device 20 can include a support member 22, an actuator 24, a first retention member or portion 26 and a second retention member or portion 28. The support member 22 can include a proximal portion 30, a central portion 32 and a distal portion 34. The central portion 32 of the support member 22 is configured to be disposed at least partially between adjacent spinous processes S1 and S2.

The medical device 20 can have a first configuration (shown in FIG. 1) and a second configuration (shown in FIG. 2). In the first configuration, the first retention member 26 and the second retention member 28 do not extend substantially outside of an outer surface or outer perimeter of the support member 22, or can otherwise have a narrow profile to allow for side implantation. In the first configuration, the medical device 20 is also referred to as being in a collapsed configuration or an undeployed configuration. The medical device 20 can be moved from the first configuration to the second configuration as shown in FIG. 2.

In the second configuration, the first retention member 26 and the second retention member 28 are in an expanded or deployed configuration. In some embodiments, as the medical device 20 is moved between the first configuration and the second configuration, a length of the support member 22 remains unchanged. In such an embodiment, a configuration of each of the first and second retention members 26 and 28 is changed, but the support member 22 remains substantially unchanged. In some embodiments, a length of the implant 20 does not substantially change as the implant 20 is moved between the first configuration and the second configuration. The implant 20 can be positioned between the adjacent spinous processes S1 and S2 such that the first and second retention members 26 and 28 can be positioned to limit lateral movement of implant 20 with respect to the spinous processes S1 and S2. For example, the first retention member 26 and the second retention member 28 can be moved to the second configuration such that the first retention portion 26 and the second retention portion 28 can each engage an outer lateral surface of the spinous processes S1 and S2 (i.e., either directly or through surrounding tissue (not shown)). As used herein the use of the terms first configuration (e.g., collapsed or undeployed) and second configuration (e.g., expanded or deployed) can refer to the medical device 20 (also referred to herein as "implant" or "spinal implant") and/or the retention members 26 and 28. To aid in the placement or orientation of the implant 120 relative to the adjacent spinous processes S1 and S2, the implant 20 can optionally include a radiopaque marker or radiopaque portion that can be viewed by the user (e.g., medical practitioner) on an imaging device during implantation. In some embodiments, proper orientation of the implant 120 can be based on the attachment of the implant 120 to an insertion and/or actuation tool (described below).

The actuator 24 is used to move the implant 20 between the first configuration and the second configuration. The actuator 24 can be movably disposed at least partially within an interior region (not shown in FIGS. 1 and 2) of the support member 22, and can be rotated relative to the support member 22. For example, an actuation tool 23, such as a medical screw driver, can be used to rotate the actuator 24. The actuation tool 23 can engage a head of the actuator 24 as described in more detail below and can be used to rotate the actuator 24 in a first direction A (e.g., clockwise) and a second direction B (e.g., counterclockwise) as shown in FIG. 2. The actuation tool 23 can be releasably engagable with the actuator 24 with known coupling methods to allow for the actuation tool 23 to be released from the implant 20 after inserting and moving the implant 20 to the second configuration. For example, a distal end portion of the actuation tool 23 can be configured to be inserted into a mating opening (e.g., slotted, hexagon shaped, star shaped, etc.) in the head of the actuator 24. In some embodiments, the actuation tool 23 can alternatively, or in addition to, be configured to receive the head of the actuator 24 within an opening in the actuation tool 23. The actuation tool 23 can be used for both insertion and actuation. Various types of insertion and/or actuation tools can be used to insert and actuate the implant 20. In some embodiments, a single tool is used for both insertion and actuation of the implant 20. In some embodiments, separate tools are used.

The first retention member 26 and the second retention member 28 can be a variety of different forms. The first retention member 26 and the second retention member 28 can each be formed with, for example, a malleable or flexible material. In some embodiments, the first retention member 26 and the second retention member 28 are formed with a shape-memory material, such as Nitinol or super-Nitinol. In some embodiments, the first retention member 26 and the second retention member 28 can be biased in a collapsed configuration and moved to an expanded configuration. In some embodiments, the first retention member 26 and the second retention member 28 can be biased in an expanded configuration and moved to a collapsed configuration. In some embodiments, the first retention member 26 and the second retention member 28 are not formed with a bias, but rather can be moved between a collapsed configuration and an expanded configuration.

In some embodiments, the first retention member 26 and the second retention member 28 are elongate and each includes a first end and a second end. In such an embodiment, the first end of each retention member 26 and 28 can be coupled to the actuator 24 and the second end of each retention member 26 and 28 can be fixedly coupled to the actuator 24 or to the support member 22. As the actuator 24 is rotated, the first end of each retention member 26 and 28 is moved relative to a position of the second end of each retention member 26 and 28. As the first end of each retention member 26 and 28 moves relative to the second end of each retention member 26 and 28, the retention members 26 and 28 are moved between the first configuration (e.g., collapsed or undeployed) and the second configuration (e.g., expanded or deployed). In some embodiments, the first end of each retention member 26 and 28 moves substantially parallel to a centerline of the actuator and/or a centerline of the support member 22. In some embodiments, the first end of each retention member 26 and 28 moves along a curved path. For example, the first end of each retention member 26 and 28 can move about a centerline of the support member 22 and/or the actuator 24.

In some embodiments, the first end of each of the first retention member 26 and the second retention member 28 are coupled to an actuation member or portion (not shown in FIGS. 1 and 2) that threadedly engages a threaded portion of the actuator 24. For example, the actuator 24 can include a threaded portion configured to engage both a first actuation member coupled to the first retention member 26 and a second actuation member coupled to the second retention member 28. In some embodiments, the actuator 24 can include two threaded portions. For example, a first threaded portion can engage the first actuation member and the second threaded portion can engage the second actuation member. The first threaded portion can have threads angled in a first direction, and the second threaded portion can have threads angled in a second opposite direction. In such an embodiment, as the actuator 24 is rotated, the first actuation member (and the first end of the first retention member 26) moves in a first direction and the second actuation member (and first end of the second retention member 28) moves in a second direction opposite the first direction.

In some embodiments, the first retention member 26 and the second retention member 28 are formed monolithically with the support member 22. The first retention member 26 and the second retention member 28 can each include a living hinge portion that allows the first retention member 26 and the second retention member 28 to be moved between the first configuration and the second configuration. For example, a first actuation member or portion (not shown in FIGS. 1 and 2) can be disposed on the actuator 24 at a first location associated with the first retention member 26 (e.g., within an interior region defined by the first retention member 26), and a second actuation member or portion (not shown in FIGS. 1 and 2) can be disposed on the actuator 24 at a second location associated with the second retention member 28 (e.g., within an interior region defined by the first retention member 26). As the actuator 24 is rotated, the first actuation member and the second actuation member are moved into engagement with and apply a force to the living hinge portions of the first retention member 26 and the second retention member 28. The force moves the first and second retention members 26 and 28 to their respective second configurations. The details of such an embodiment are described below with reference to FIGS. 23 and 24.

In some embodiments, the support member 22 defines openings on an outer wall that are in communication with an interior region of the support member 22. In such an embodiment, the first retention member 26 and the second retention member 28 can each be moved through a respective opening when moved between the first configuration and the second configuration. The openings can be a variety of different sizes and shapes. For example, the openings can be round, oval, rectangular, triangular, elliptical, or square.

Various types of insertion and/or deployment tools (e.g., actuation tools) can be used to insert the implant 20 into a patient's body. Examples of some deployment tools are described in U.S. patent application Ser. No. 11/454,153, filed Jun. 16, 2006, and entitled "Percutaneous Spinal Implants and Methods," the disclosure of which is hereby incorporated by reference in its entirety. In some embodiments, the deployment tool can also be configured to rotate the actuator such that a single insertion and actuation tool can be used.

In use, the spinous processes S1 and S2 can be distracted prior to inserting the medical device 20. For example, a medical device configured to be temporarily inserted between the spinous processes S1 and S2 and used to distract (e.g., spread apart) the spinous processes S1 and S2 to provide space for insertion of the medical device 20. When the spinous processes are distracted, a trocar, for example, can be used to define an access passage for the medical device 20. In some embodiments, the trocar can be used to define the passage as well as distract the spinous processes S1 and S2. Once an access passage is defined, the medical device 20 (also referred to herein as "implant" or "spinal implant") can be inserted percutaneously (i.e., through an opening in the skin) and in a minimally-invasive manner and advanced between the spinous processes S1 and S2 with the first retention member 26 and the second retention member 28 in the first configurations (as shown in FIG. 1). The distal end portion 34 of the support member 22 is inserted first and advanced until at least a portion of the central portion 32 of the support member 22 is located between the spinous processes S1 and S2. In some embodiments, the size of the opening/incision in the skin can be, for example, between 3 millimeters in length and 25 millimeters in length.

Once the central portion 32 of the support member 22 is in place between the spinous processes S1 and S2, the first retention member 26 and the second retention member 28 are moved to the second configuration (as shown in FIG. 2) as described above (e.g., by rotating the actuator 24 in a first direction, e.g., clockwise). In the second configuration (e.g., expanded), a size (e.g., outer perimeter, diameter or height in an end view of the implant) of the retention members 26 and 28 is greater than the space between the adjacent spinous process S1 and S2. Thus, the first retention member 26 and the second retention member 28 in the second configuration can limit lateral movement of the implant 20 relative to the adjacent spinous processes S1 and S2 and the central portion 32 of the support member 22 can limit extension or prevent over-extension of the spinous processes S1 and S2. In some embodiments, the central portion 32 can contact the adjacent spinous processes S1 and S2 (which may include the surrounding tissue) when the spinous processes S1 and S2 are in flexion. In some embodiments the central portion 32 can maintain a space between the adjacent spinous processes S1 and S2, thus alleviating compressive forces that could lead to problems such as spinal stenosis.

To remove or reposition the implant 20, the actuator 24 is rotated in a second direction opposite the first direction (e.g., counterclockwise). This action will move the first retention member 26 and the second retention member 28 back to the first configuration (e.g., collapsed). Thus, the implant 20 can be repeatedly moved between a collapsed configuration and an expanded configuration as needed.

FIGS. 3-7 illustrate an embodiment of a medical device 120. The medical device 120 (also referred to herein as "implant" or "spinal implant") includes a support member 122, an actuator 124, a first retention member 126 and a second retention member 128. The support member 122 includes a proximal portion 130, a central portion 132 and a distal portion 134, and defines an interior region 136 within which the actuator 124 is at least partially disposed as shown in FIGS. 5A and 5B. Specifically, the actuator 124 is movably coupled to mounting brackets 137 and 138 within the interior region 136 of the support member 122. For example, the actuator 124 can rotate relative to the mounting brackets 137 and 138 and the support member 122.

The actuator 124 includes a first threaded portion 139 and a second threaded portion 140. The first threaded portion includes threads angled in a first direction, and the second threaded portion 140 has threads angled in a second direction, opposite the first direction. The first threaded portion 139 is configured to threadedly engage a first actuation member 142, and the second threaded portion 140 is configured to threadedly engage a second actuation member 144.

Figure 5A:
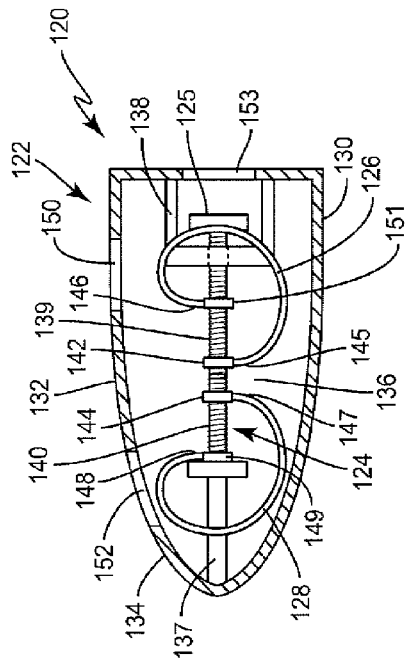
FIG. 5A is a partial side cross-sectional view of the medical device of FIGS. 3 and 4 taken along line 5-5 in FIG. 4 and shown in the first configuration.
Figure 5B:
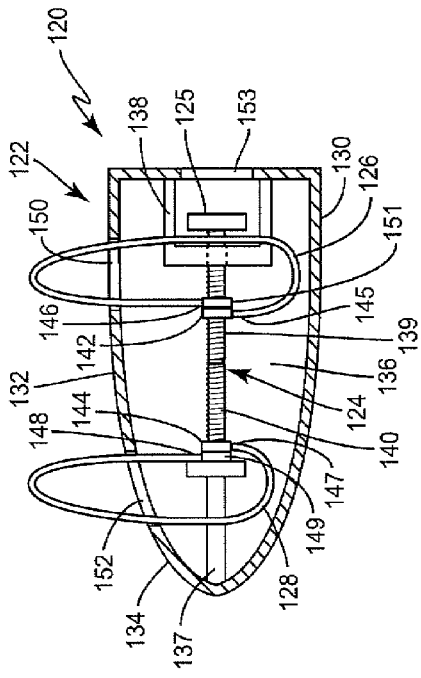
FIG. 5B is a partial cross-sectional view of the medical device of FIGS. 3 and 4 taken along line 5-5 in FIG. 4 and shown in a second configuration.
Figure 3:
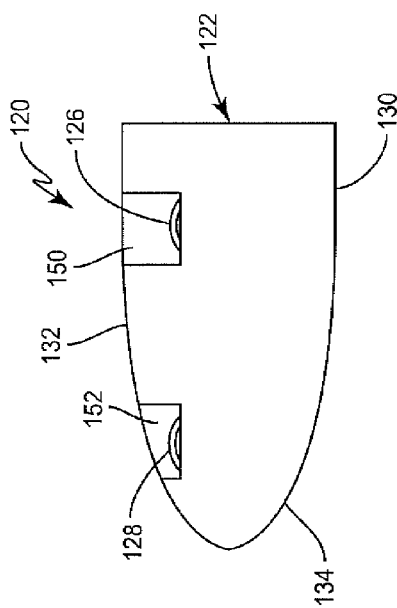
FIG. 3 is a side view of a medical device according to an embodiment shown in a first configuration.

The first retention member 126 has a first end 145 coupled to the first actuation member 142, and a second end 146 coupled to the actuator 124. The second retention member 128 has a first end 147 coupled to the second actuation member 144, and a second end 148 coupled to the actuator 124. When the actuator 124 is rotated relative to the support member 122, the first actuation member 142 moves between a first position (as shown in FIG. 5A) and a second position (as shown in FIG. 5B), and the second actuation member 144 moves between a first position (as shown in FIG. 5A) and a second position (as shown in FIG. 5B). In this embodiment, the first actuation member 142 and the second actuation member 144 move along a path substantially parallel to a centerline of the actuator 124 and/or support member 122. Thus, as the actuator 124 is rotated, the first end 145 of the first retention member 126 moves with the first actuation member 142 and the first end 147 of the second retention member 128 moves with the second actuation member 144. The second end 146 of the first retention member 126 and the second end 148 of the second retention member 128 are coupled to the actuator 124 such that as the actuator 124 is rotated, they each maintain their longitudinal positions. For example, the second end 146 of the first retention member 126 can be coupled to a bushing (or bearing assembly) 151 through which the first threaded portion 139 of the actuator 124 is received, and the second end 148 of the second retention member 128 can be coupled to a bushing (or bearing assembly) 149 through which the second threaded portion 140 of the actuator 124 is received. The bushing 151 and the bushing 149 can provide a friction fit to the actuator 124 while allowing the actuator 124 to rotate relative to each of the bushings 149 and 151. In some embodiments, the bushings 149 and 151 can be fixedly coupled to the support member 122. As shown in FIGS. 5A and 5B, because of the oppositely angled threads on the first threaded portion 139 and the second threaded portion 140, the first actuation member 142 moves in a first direction while simultaneously, the second actuation member 144 moves in a second direction opposite the first direction.

Also as shown in FIGS. 5A and 5B, the first end 145 of the first retention member 126 moves from a first position relative to the second end 146 of the first retention member 126 (shown in FIG. 5A) to a second position relative to the second end 146 of the first retention member 126 (shown in FIG. 5B). Similarly, the first end 147 of the second retention member 128 moves from a first position relative to the second end 148 of the second retention member 128 (shown in FIG. 5A) to a second position relative to the second end 148 of the second retention member 128 (shown in FIG. 5B). As the first end 145 of the first retention member 126 moves from its first position to its second position relative to the second end 146 of the first retention member 126, a portion of the retention member 126 is moved outside of an opening 150 defined by the support member 122. Likewise, as the first end 147 of the second retention member 128 moves from its first position to its second position relative to the second end 148 of the second retention member 128, a portion of the retention member 128 is moved outside of an opening 152 defined by the support member 122. Thus, when the first retention member 126 and the second retention member 128 can each be moved between a first configuration (e.g., collapsed or undeployed) and a second configuration (e.g., (expanded or deployed). As used herein the use of the terms first configuration (e.g., collapsed or undeployed) and second configuration (e.g., expanded or deployed) can refer to the implant 120 and/or the retention members 126 and 128.

The first retention member 126 and the second retention member 128 can each be formed with, for example, a malleable or flexible material, such as Nitinol or super Nitinol, having shape-memory properties, which can aid in deployment of the first and second retention members 126, 128 from the first configuration to the second configuration. For example, such materials can allow each of the first retention member 126 and the second retention member 128 to be collapsed within the interior region 136 of the support member 122 and then moved to a biased expanded configuration as they are each moved outside of the respective openings 150 and 152 of the support member 122. In some embodiments, the first and second retention members 126 and 128 can be formed with shape memory materials such that they are self actuating.

Figure 6:
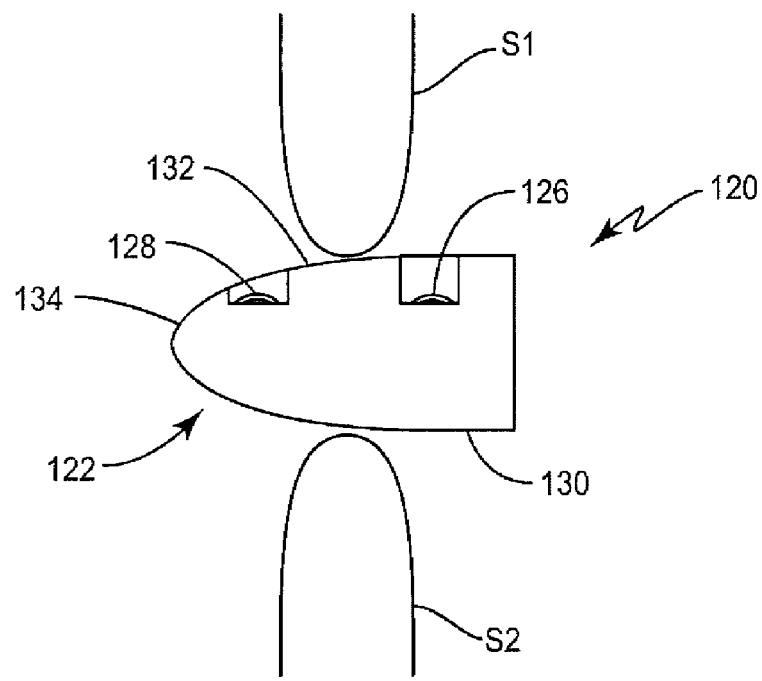
FIG. 6 is a posterior view of the medical device of FIG. 3 shown in the first configuration adjacent two adjacent spinous processes.

In use, the implant 120 can be inserted between anatomical structures, such as between adjacent spinous processes and used to limit extension of the adjacent spinous processes as described above for implant 20. For example, as shown in FIG. 6, the implant 120 can be inserted into a space between the spinous processes S1 and S2 while in a first configuration (e.g., collapsed or undeployed), as described above for medical device 20. As described above, the implant 120 can optionally include a radiopaque marker or radiopaque portion to help guide the implant 120 to a desired location relative to the adjacent spinous processes S1 and S2. In some embodiments, proper orientation of the implant 120 can be based on the attachment of the implant 120 to an insertion/actuation tool.

Figure 7:
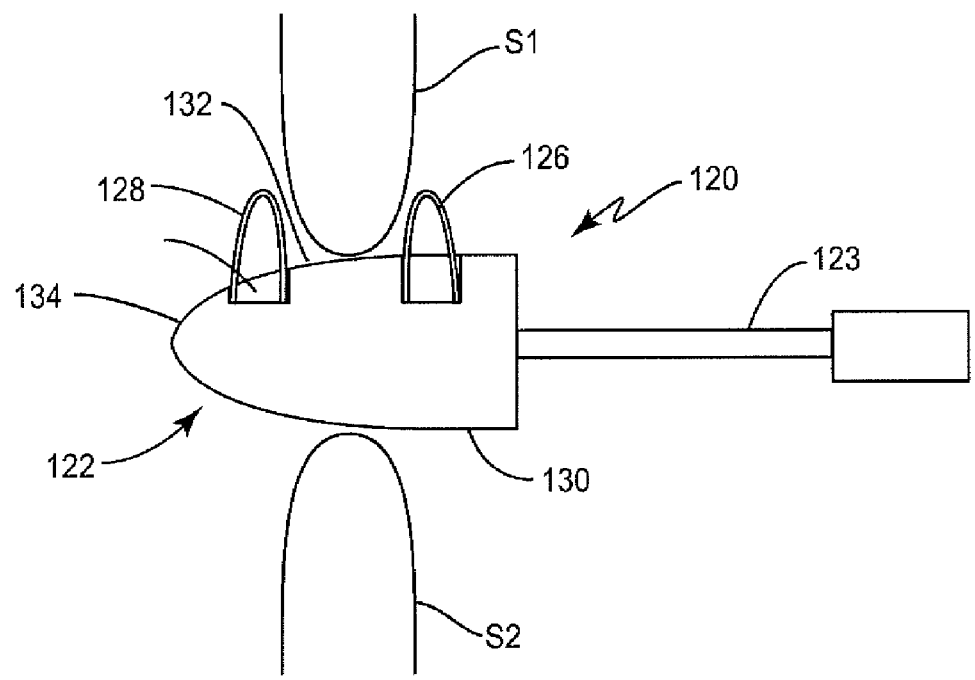
FIG. 7 is a posterior view of the medical device of FIG. 3 shown in the second configuration adjacent two adjacent spinous processes.

After placing the implant 120 in a desired position, the implant 120 can be moved to a second configuration (e.g., expanded or deployed) as shown in FIG. 7. For example, an actuation tool 123, such as a medical screw driver, can be inserted through an opening 153 defined by the support member 122, and engage a head portion 125 of the actuator 124. The actuator 124 can then be rotated in a first direction (e.g., clockwise), which will move a portion of the first retention member 126 outside of the opening 150, and a portion of the second retention member 128 outside the opening 152 as described above. In this configuration, the central portion 132 of the support member 122 can limit extension of the spinous processes S1 and S2, and the first retention member 126 and the second retention member 128 are sufficiently sized to limit lateral movement of the implant 120 relative to the spinous processes S1 and S2.

Figure 4:
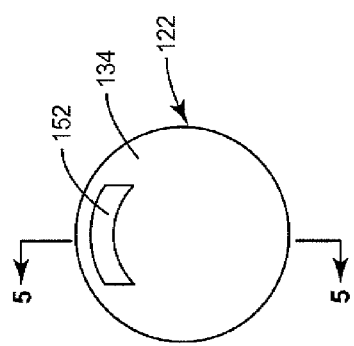
FIG. 4 is a distal end view of the medical device of FIG. 3 shown in the first configuration.

To remove or reposition the implant 120, the actuation tool 123 can be used to rotate the actuator 124 in a second direction opposite the first direction (e.g., counterclockwise). This action will move the first actuation member 142 and the second actuation member 144 to their respective first positions, and collapse the first retention member 126 and the second retention member 128 within the interior region 136 of the support member 122, as shown in FIG. 4. Thus, the implant 120 can be repeatedly moved between a collapsed configuration and an expanded configuration as needed.

Figure 26:
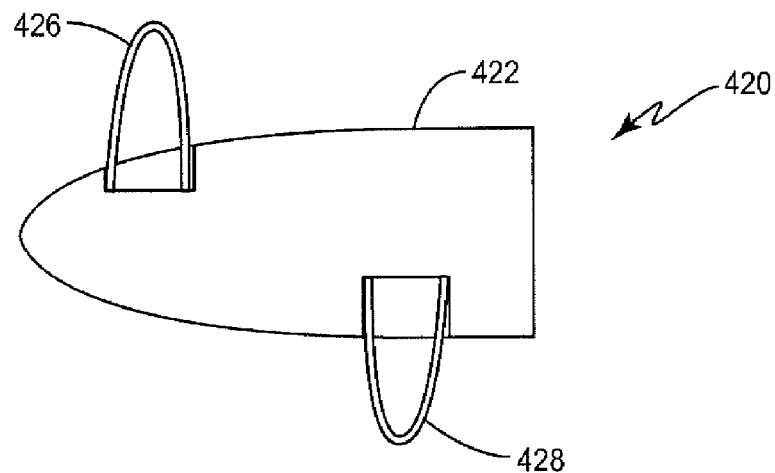
FIGS. 26-28 are each a side view of a different embodiment of a medical device, shown in an expanded configuration.
Figure 27:
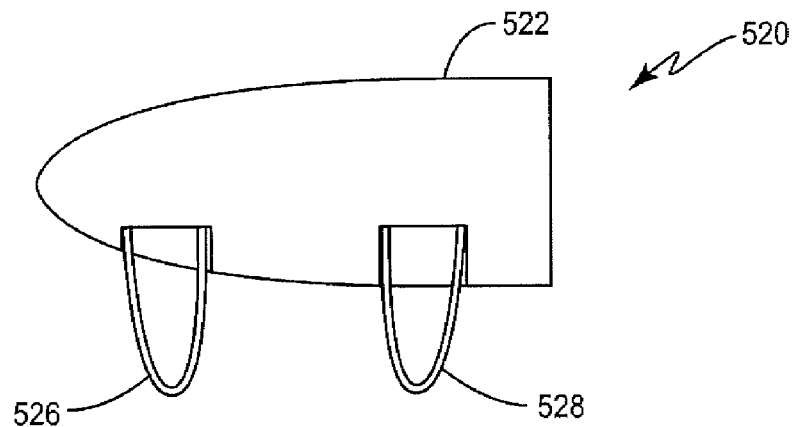
Figure 28:
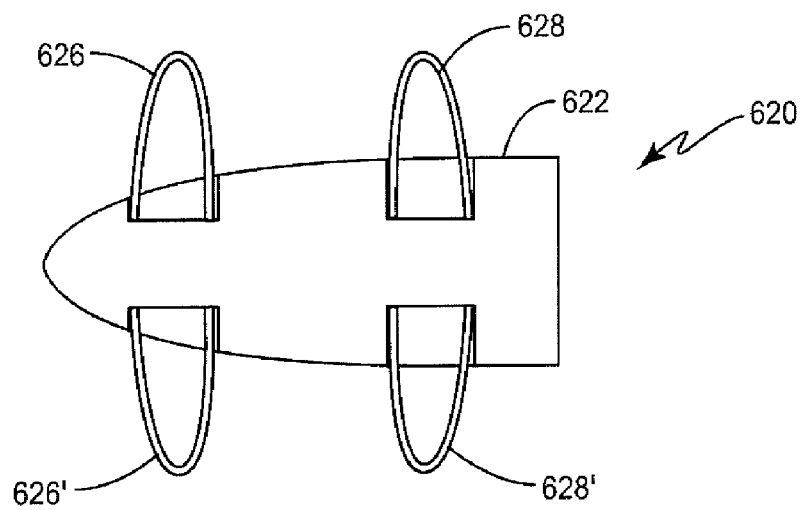

Although FIGS. 2-7 illustrate a first retention member 126 and a second retention member 128 each being movable from a first configuration (e.g., collapsed or undeployed) and a second configuration (e.g., expanded or deployed) substantially symmetrically and on the same side of the support member 122 (e.g., as the retention members 126 and 128 are shown in FIG. 5B), other embodiments can include different configurations. For example, as shown in FIG. 26, an implant 420 can include a first retention member 426 deployable to an expanded configuration above or on a top side of a support member 422, and a second retention member 428 deployable to an expanded configuration below or on a bottom side of the support member 422. In another example shown in FIG. 27, an implant 520 includes a first retention member 526 and a second retention member 528 both deployable to an expanded configuration below or on a bottom side of a support member 522. In addition, although two retention members are shown and described in FIGS. 2-7, an implant can include more than two retention members. For example, as shown in FIG. 28, an implant 620 includes two retention members 626 and 628 each deployable on a top side of a support member 622 and two retention members 626' and 628' deployable on a bottom side of the support member 622.

Figure 8:
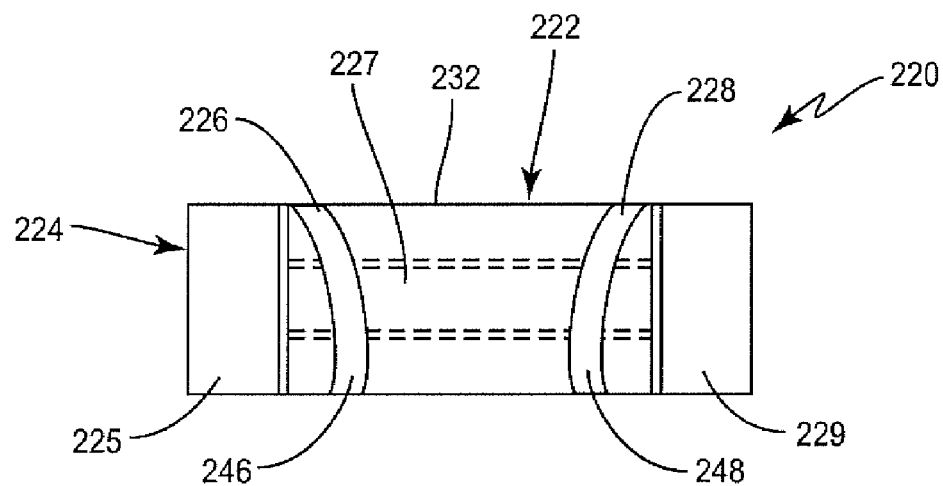
FIG. 8 is a side view of a medical device according to another embodiment shown in a first configuration.
Figure 9:
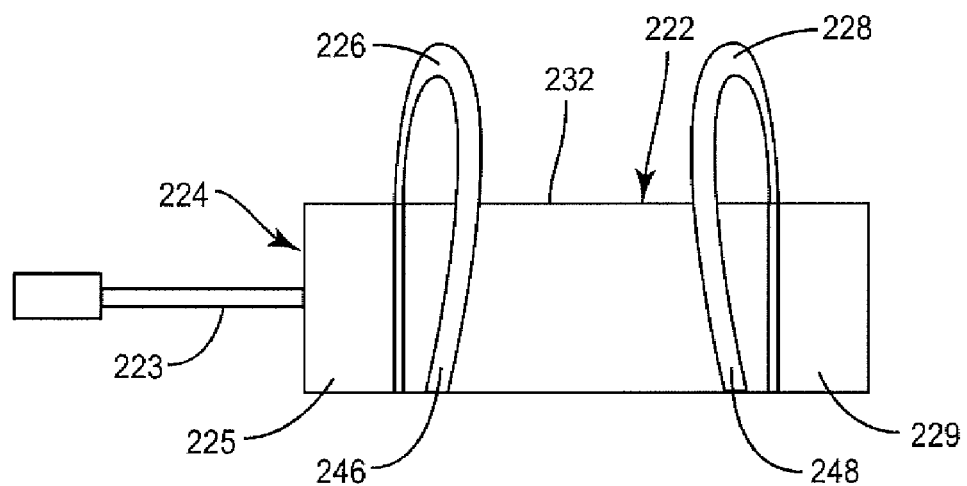
FIG. 9 is a side view of the medical device of FIG. 8 shown in a second configuration.

FIGS. 8-22 illustrate a medical device according to another embodiment. A medical device 220 (also referred to herein as "implant") includes a support member 222, an actuator 224, a first retention member 226 and a second retention member 228. The support member 222 defines an interior region 236 (shown in FIGS. 8 and 10) within which at least a portion of the actuator 224 is disposed. The actuator 224 is movably coupled to the support member 222 such that the actuator 224 can rotate relative to the support member 222. The support member 222 also includes a central portion 232 as shown in FIGS. 8 and 9.

In this embodiment, the actuator 224 includes a proximal end portion 225, an elongate portion 227 and a distal end portion 229. As with the previous embodiments, the actuator 224 is used to move the implant 220 between a first configuration (e.g., collapsed or undeployed) as shown in FIG. 8, and a second configuration (e.g., expanded or deployed) as shown in FIG. 9. As used herein the use of the terms first configuration (e.g., collapsed or undeployed) and second configuration (e.g., expanded or deployed) can refer to the implant 220 and/or the retention members 226 and 228. Thus, the retention members 226 and 228 can each be moved between a first configuration and a second configuration, which in turn, moves the implant 220 between its first configuration and second configuration.

Figure 10:
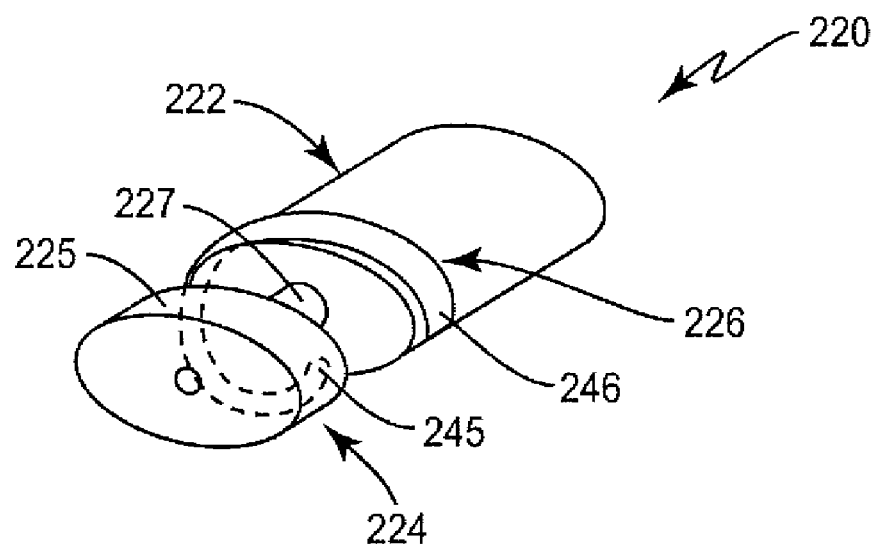
FIG. 10 is an exploded side perspective view of a proximal end portion of the medical device of FIG. 8 shown in the first configuration.
Figure 11:
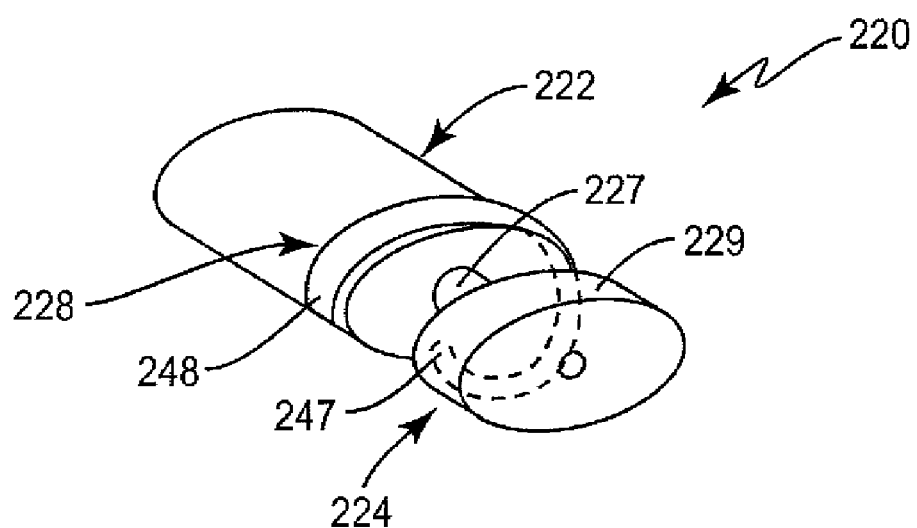
FIG. 11 is an exploded side perspective view of a distal end portion of the medical device of FIG. 8 shown in the first configuration.

The first retention member 226 has a first end 245 coupled to the proximal end portion 225 of the actuator 224, and a second end 246 fixedly coupled to the support member 222. The second retention member 228 has a first end 247 coupled to the distal end portion 229 of the actuator 224, and a second end 248 fixedly coupled to the support member 222. FIG. 10 is a partially exploded view of a proximal end portion of the implant 220 in the first configuration (e.g., collapsed or undeployed) and FIG. 11 is a partially exploded view of a distal end portion of the implant 220 in the first configuration (e.g., collapsed or undeployed) each illustrating the coupling of the first retention member 226 and the second retention member 228 to the actuator 224 and the support member 222.

FIGS. 12-18 illustrate the movement of the implant 220 between the first configuration and the second configuration. Only a proximal end portion of the implant 220 is shown in FIGS. 12-18 for illustration purposes. FIGS. 12 and 13 illustrate the implant 220 in the first configuration (e.g., collapsed or undeployed); FIG. 12 is a perspective view of a proximal end portion of the implant 220 and FIG. 13 is a proximal end view of the implant 220. When the actuator 224 is rotated relative to the support member 222 in a first direction A (e.g., clockwise as shown in FIGS. 14-17), the first end 245 of the first retention member 226 moves along a curved path relative to the second end 246 of the retention member 226. For example, the first end 245 rotates about a centerline of the actuator 224 and/or the support member 222. The curved path can include a spiral configuration. The first end 245 of the first retention member 226 moves between various distances relative to the second end 246 of the first retention member 226 and the second end 246 remains fixed relative to the support member 222. For example, FIG. 14 shows the actuator 224 rotated 90 degrees relative to the support member 222; FIG. 15 shows the actuator 224 rotated 180 degrees relative to support member 222; and FIG. 16 shows the actuator 224 rotated 270 degrees relative to the support member 222. FIGS. 17 and 18 each show the actuator 224 rotated 360 degrees relative to the support member 222; FIG. 17 is a proximal end view of the implant 220 and FIG. 18 is a side perspective view of the proximal end portion of the implant 220.

As shown in FIGS. 14-17, during the progressive rotation of the actuator 224 relative to the support member 222, the first end 245 of the first retention member 226 moves relative to the second end 246 of the first retention member 226, while the second end 246 of the first retention member 226 remains stationary or at a fixed position relative to the support member 222. For example, the first end 245 is at a first distance d1 from the second end 246 as shown in FIG. 13, at a second distance d2 shown in FIG. 15 and at a third distance d3 shown in FIG. 17. In some embodiments, the distance d1 is substantially the same as the distance d3. In some embodiments, the distance d2 is greater than the distance d1. As the first end 245 moves relative to the second end 246, a portion of the first retention member 226 is moved to varying distances extending from an outer surface of the support member 222. Thus, the actuator 224 can be rotated incrementally to achieve a desired size (e.g., outer profile or outer perimeter) of the overall implant 220 as needed for a particular use or embodiment.

Figure 19:
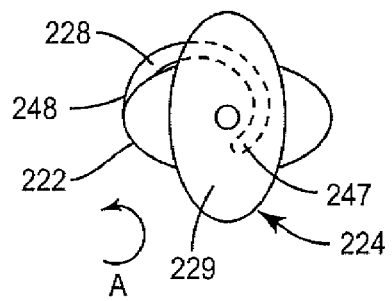
FIG. 19 is a distal end view of the medical device of FIG. 8 with the actuator shown rotated 90 degrees relative to the support member.
Figure 20:
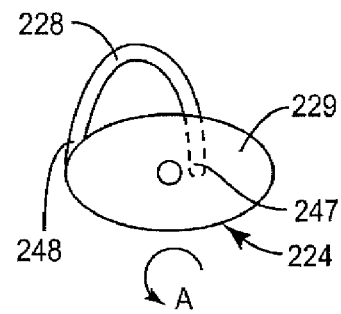
FIG. 20 is a distal end view of the medical device of FIG. 8 with the actuator shown rotated 180 degrees relative to the support member.
Figure 21:
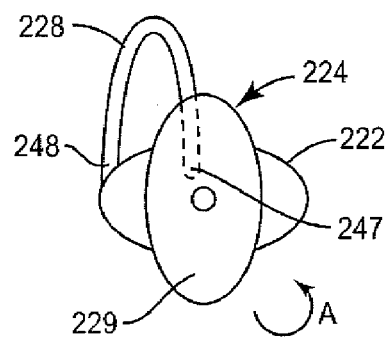
FIG. 21 is a distal end view of the medical device of FIG. 8 with the actuator shown rotated 270 degrees relative to the support member.
Figure 22:
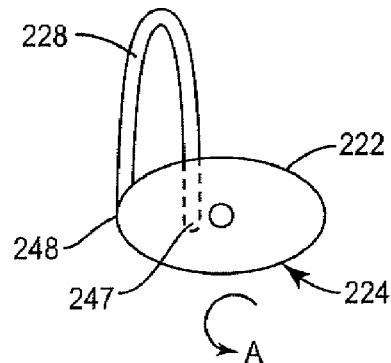
FIG. 22 is a distal end view of the medical device of FIG. 8 with the actuator shown rotated 360 degrees relative to the support member.

FIGS. 19-22 illustrate the distal end portion of the medical device as the actuator 224 is rotated relative to the support member 222. The rotational direction A (e.g., clockwise) appears to be counterclockwise in FIGS. 19-22 because these figures illustrate a view of the distal end of the implant. The rotation of the actuator 224 rotates the proximal end portion 225 (see FIG. 10), the elongate portion 227 (see FIGS. 10 and 11) and the distal end portion 229 in the same direction. As the actuator 224 is rotated, relative to the support member 222, the first end 247 of the second retention member 228 is moved relative to the second end 248 of the second retention member 228 and the second end 248 remains fixed. For example, FIG. 19 shows the actuator 224 rotated 90 degrees relative to the support member 222; FIG. 20 shows the actuator 224 rotated 180 degrees relative to support member 222; FIG. 21 shows the actuator 224 rotated 270 degrees relative to the support member 222; and FIG. 22 shows the actuator 224 rotated 360 degrees relative to the support member 222.

The first retention member 226 and the second retention member 228 can each be formed, for example, with a malleable or flexible material, such that the first retention member 226 and the second retention member 228 are sufficiently flexible to be coiled around the support member 222 (e.g., in the first configuration), yet sufficiently rigid to help limit lateral movement of the implant 220 when deployed within a patient's body (e.g., in the second configuration).

As with the previous embodiments, the implant 220 can be inserted between anatomical structures, such as between adjacent spinous processes and used to limit extension of the adjacent spinous processes. For example, the implant 220 can be inserted into a space between the spinous processes (not shown), while in a first configuration (e.g., collapsed or undeployed) (see e.g., FIGS. 8, 12 and 13), such that the central portion 232 of the support member 222 is disposed between the adjacent spinous processes, as described above for medical device 120. After placing the implant 220 in a desired position, the implant 220 can be moved to the second configuration (e.g., expanded or deployed) (see e.g., FIGS. 9, 18 and 22). For example, an actuation tool 223 (shown in FIG. 9), such as a medical screw driver, can engage the proximal end portion 225 of the actuator 224 as previously described. The actuator 224 can then be rotated in a first direction (e.g., clockwise), which will move the first retention member 226 and the second retention member 228 to the second configuration (e.g., expanded or deployed) as described above. In this configuration, the central portion 232 (see e.g., FIGS. 8 and 9) of the support member 222 can limit extension of the spinous processes, and the first retention member 226 and the second retention member 228 can limit lateral movement of the implant 220 relative to the spinous processes.

To remove or reposition the implant 220, the actuation tool 223 can be used to rotate the actuator 224 in a second direction opposite the first direction (e.g., counterclockwise). This action will move the first retention member 226 and the second retention member 228 to the second configuration (e.g., collapsed or undeployed). Thus, as with the previous embodiments, the implant 220 can be repeatedly moved between a collapsed configuration and an expanded configuration as needed.

Figure 23:
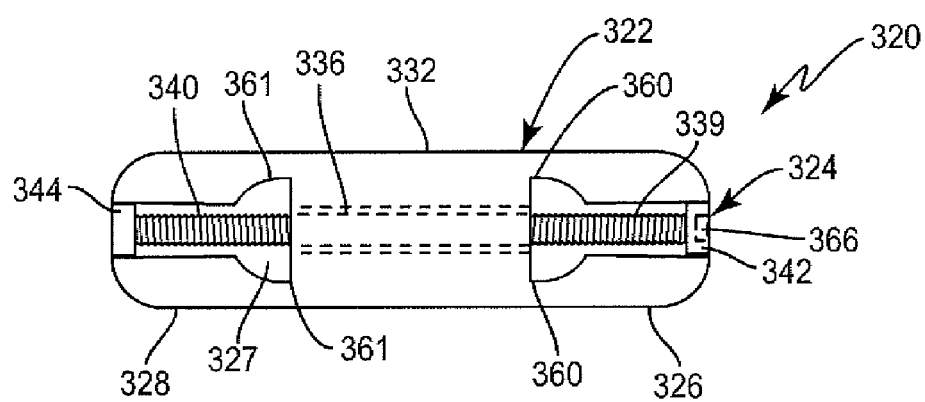
FIG. 23 is a side view of a medical device according to another embodiment shown in a first configuration.
Figure 24:
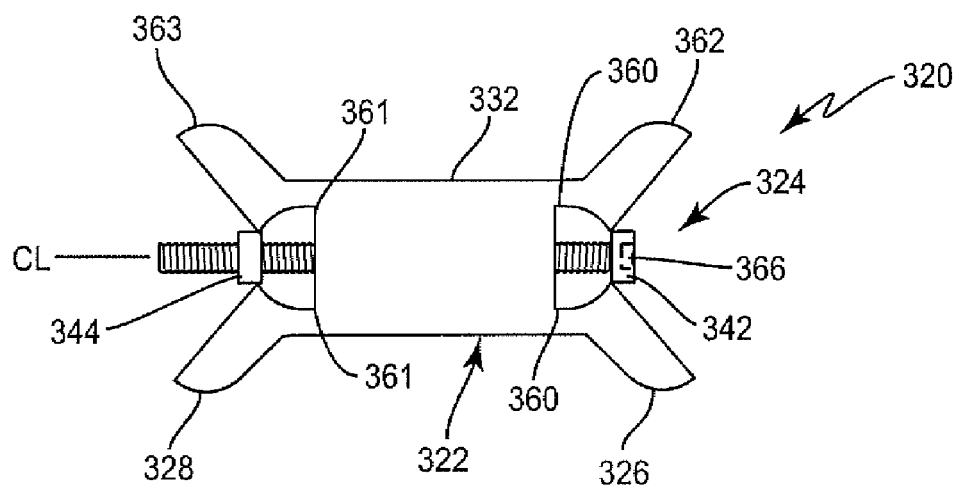
FIG. 24 is a side view of the medical device of FIG. 23 shown in a second configuration.

FIGS. 23 and 24 illustrate another example embodiment of a medical device. A medical device 320 (also referred to herein as "implant" or "spinal implant") includes a support member 322, an actuator 324, a first retention member or portion 326 and a second retention member or portion 328. The support member 322 defines an interior region 336 within which the actuator 324 is at least partially disposed and defines a central portion 332 configured to engage anatomical structures as shown in FIG. 23. The actuator 324 is movably coupled to the support member 322 such that the actuator 324 can rotate relative to the support member 322.

The actuator 324 (also referred to herein as "actuation assembly") includes an elongate portion 327 having a first threaded portion 339 and a second threaded portion 340. The first threaded portion 339 includes threads angled in a first direction, and the second threaded portion 340 has threads angled in a second direction, opposite the first direction. The first threaded portion 339 is configured to threadedly engage a first actuation member or portion 342, and the second threaded portion 340 is configured to threadedly engage a second actuation member or portion 344. The first actuation member 342 and can be formed monolithically with the elongate portion 327 or can be a separate component. The first actuation member 342 is fixed or stationary relative to the elongate portion 327. The first actuation member 342 also includes an engagement portion 366 configured to be engaged by an actuation tool, such as a medical screw driver (not shown in FIGS. 23 and 24).

In this example embodiment, the first retention member 326 and the second retention member 328 are shown formed monolithically with the support member 322. It should be understood, however, that the first retention member 326 and the second retention member 328 can alternatively be separate components coupled to the support member 322. The first retention member 326 defines a first living hinge portion 360 and includes deformable arms 362. The second retention member 328 defines a second living hinge portion 361 and includes deformable arms 363. FIGS. 23 and 24 illustrate two deformable arms 362 and two deformable arms 363, but it should be understood that the number of deformable arms can vary. For example, there can be three, four, five, six, etc. In addition, the shape and size of the deformable arms 362 and 363 can also vary. The living hinge portions 360 and 361 enable the first retention member 326 and the second retention member 328, respectively, to be moved from a first configuration (e.g., collapsed or undeployed), as shown in FIG. 23, and a second configuration (e.g., expanded or deployed), as shown in FIG. 24.

When the actuator 324 is rotated relative to the support member 322, the first actuation member 342 (and the elongate portion 327) moves between a first position as shown in FIG. 23 and a second position as shown in FIG. 24. Simultaneously, because of the oppositely angled threaded portions 339 and 340, the second actuation member 344 moves between a first position as shown in FIG. 23 and a second position as shown in FIG. 24. In other words, the second actuation member 344 is drawn along the second threaded portion 340 of the elongate portion 327 in an opposite direction as the movement of the first actuation member 342. In this embodiment, the first actuation member 342 and the second actuation member 344 move in a direction substantially parallel to a centerline of the actuation member 324 and/or a centerline of the support member 322.

As the first actuation member 342 and the second actuation member 344 are each moved from their respective first positions (FIG. 23) to their respective second positions (FIG. 24), they apply a force on the living hinge portions 360 and 361, respectively. Specifically, as the first actuation member 342 and the second actuation member 344 are moved to their respective second positions, they force the deformable arms 360 and 361 outwardly in a direction away from a centerline CL of the implant, and the first retention member 326 and the second retention member 328 move from the first configuration (e.g., collapsed or undeployed) to the second configuration (e.g., expanded or deployed). As described above, the terms first configuration (e.g., collapsed or undeployed) and second configuration (e.g., expanded or deployed) can refer to the implant 320 and/or the retention members 326 and 328.

The first retention member 326 and the second retention member 328 can each be formed with a material having shape memory properties, such that the first retention member 326 and the second retention member 328 are biased into the first configuration (e.g., collapsed or undeployed) and can be moved to the second configuration (e.g., expanded or deployed) as described above. The shape memory properties of the material allow the implant 320 to be repeatedly moved between the first and second configurations.

In use, the implant 320 can be inserted between anatomical structures, such as between adjacent spinous processes, and used to limit extension of the spine at the adjacent spinous processes. For example, the implant 320 can be inserted into a space between the spinous processes while in the first configuration (e.g., collapsed or undeployed) (FIG. 23), as described above for previous embodiments. After placing the implant 320 in a desired position (e.g., with the central portion 332 of the support member 322 in a space between the anatomical structures), the implant 320 can be moved to the second configuration (e.g., expanded or deployed) (FIG. 24). For example, a medical tool (not shown), such as a medical screw driver, can engage the engagement portion 366 of the first actuation member 342. The actuator 324 can then be rotated in a first direction (e.g., clockwise), which moves the first retention member 326 and the second retention member 328 to their respective second configurations as described above. In the second configuration, the central portion 332 of the support member 322 can limit extension of the spinous processes, and the first retention member 326 and the second retention member 328 can limit lateral movement of the implant 320 relative to the spinous processes.

To remove or reposition the implant 320, the medical tool can be used to rotate the actuator 324 in a second direction opposite the first direction (e.g., counterclockwise). This rotation will move the first actuation member 342 and the second actuation member 344 to their respective first positions, and move the first retention member 326 and the retention member 328 to their respective first configurations. Thus, the implant 320 can be repeatedly moved between a collapsed configuration and an expanded configuration as needed.

The various components of the implants (e.g., 20, 120, 220, 320, 420, 520, 620) described herein can be constructed with various biocompatible materials such as, for example, titanium, titanium alloyed, surgical steel, biocompatible metal alloys, stainless steel, Nitinol, super-Nitinol, plastic, polyetheretherketone (PEEK), carbon fiber, ultra-high molecular weight (UHMW) polyethylene, biocompatible polymeric materials, etc. The material of a central portion of the implant can have, for example, a compressive strength similar to or higher than that of bone. In one embodiment, the central portion of the implant, which is placed between the two adjacent spinous processes, is configured with a material having an elastic modulus higher than the elastic modulus of the bone, which forms the spinous processes. In another embodiment, the central portion of the implant is configured with a material having a higher elastic modulus than the materials used to configure the distal and proximal portions of the implant. For example, the central portion of the implant may have an elastic modulus higher than bone, while the proximal and distal portions have a lower elastic modulus than bone. In yet another embodiment, where the implant is configured with an outer shell and an inner core.

Figure 25:
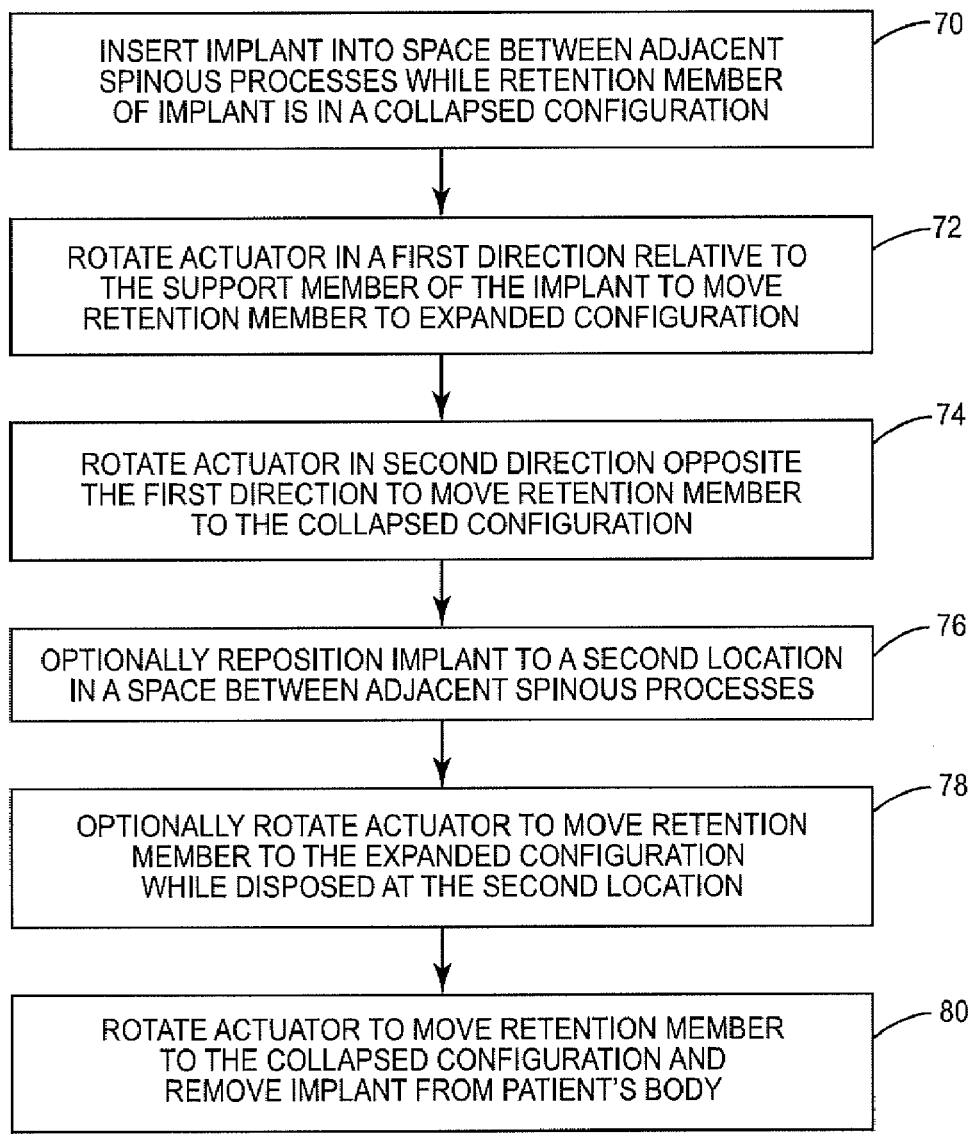
FIG. 25 is a flowchart of a method of inserting and deploying a medical device.

FIG. 25 is a flowchart illustrating a method of inserting and deploying an implant. The method includes at 70, disposing at least a portion of an implant in a space between adjacent spinous processes. For example, the implant can be inserted into the space while in a collapsed configuration as described herein. The implant can include a support member, an actuator coupled to the support member, and an elongate retention member having a first end and a second end. As described herein, the second end of the elongate retention member can be fixed to either the support member or the actuator. At 72, the actuator is rotated in a first direction relative to the support member such that the first end of the elongate retention member moves relative to the second end of the elongate retention member and the elongate retention member is moved to an expanded configuration. In some embodiments, during the rotation of the actuator, the first end of the elongate retention member is moved from a first location at a first distance from the second end of the elongate retention member to a second location at a second distance from the second end of the elongate retention member, where the first distance is non-zero and greater than the second distance.

In some embodiments, when the elongate retention member is moved to the expanded configuration, at least a portion of the elongate retention member is moved through an opening in the support member and is disposed at a non-zero distance from an outer surface of the support member. In some embodiments, when the elongate retention member is moved to the expanded configuration, at least a portion of the elongate retention member is moved through a curved path. In some embodiment, during the rotating, the first end of the elongate retention member moves in a direction substantially parallel to a longitudinal centerline of the support member.

At 74, the actuator is rotated in a second direction opposite the first direction, such that the elongate retention member is moved to a collapsed configuration. At 76, the implant can optionally be repositioned to a second location in a space between adjacent spinous processes. At 78, the actuator can be optionally rotated again to move the elongate retention member to the expanded configuration while disposed at the second location. At 80, the actuator is optionally rotated to move the elongate retention member to the collapsed configuration and the implant is removed from the patient's body.

While various embodiments have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

For example, although the embodiments above are primarily described as being spinal implants configured to be positioned in a space between adjacent spinous processes, in alternative embodiments, the implants are configured to be positioned adjacent any bone, tissue or other bodily structure where it is desirable to maintain spacing while preventing axial or longitudinal movement of the implant.

Although various embodiments have been described as having particular features and/or combinations of components, other embodiments are possible having a combination or sub-combination of any features and/or components from any of embodiments as discussed above. For example, the implant (20, 120, 220, 320, 420, 520, 620) can be configured to be actuated with a threaded actuator (e.g., 124 324) or a non-threaded actuator (e.g., 224). Further, the engagement portion of the actuator can be configured to matingly engage a variety of different types of actuation tools that can be used to rotate the actuator.

Although various implants have been shown and described above as having a first configuration and a second configuration (e.g., a collapsed configuration and an expanded configuration), in some embodiments, an implant can include three or more configurations. For example, in some embodiments, an implant can have a first configuration, in which the implant can be inserted between the spinous processes unimpeded by a retention member of the implant, a second configuration, in which lateral movement of the implant is limited by the retention member and a third configuration in which the implant can move in one lateral direction, but not the other.

In some embodiments, an actuation tool (e.g., tools 23, 123, 223), and/or an implant deployment or insertion tool can be configured to perform any combination of functions described herein. For example, in some embodiments, a deployment tool can be configured to insert a spinal implant into a body, and also used to actuate the actuator to move the spinal implant between a collapsed configuration and an expanded configuration within a body, reposition a spinal implant within the body and/or remove a spinal implant from the body. In some embodiments, such tools can be configured to perform only a single function, such as, for example, removing a spinal implant from the body. In other embodiments, a kit can be provided that includes any number of insertion tools, actuation tools, and/or implants as described herein.

Further, the various components of a medical device as described herein can have a variety of different shapes and or size not specifically illustrated. For example, the retention members can be various lengths, widths, and/or thicknesses. In another example, the actuators and/or the various portions of an actuator can be various lengths and have various cross-sections. The elongate portions of an actuator can have a lumen or can be solid depending on its particular function.

What is claimed is:

1. An apparatus, comprising:
   a support member defining a longitudinal axis and configured to be implanted at least partially into a space between adjacent spinous processes;
   an actuator coupled to the support member;
   a first elongate retention member having first and second ends mounted at a distal portion of the actuator;
   a second elongate retention member having first and second ends mounted at a proximal portion of the actuator;
   the actuator configured to be rotated relative to the support member such that the second end of the first elongate retention member maintains a longitudinal position and the first end of the first elongate retention member moves from a first location in which the first end of the first elongate retention member is at a first larger distance from the second end of the first elongate retention member to a second location in which the first end of the first elongate retention member is at a second smaller distance from the second end of the first elongate retention member;
   wherein at least a portion of the first elongate retention member is disposed a first non-zero distance from an outer surface of the support member, and external thereto, when the first end of the first elongate retention member is at its second location;
   wherein the portion of the first elongate retention member is disposed within an interior of the support member when the first end of the elongate retention member is at its first location.

2. The apparatus of claim 1, wherein the first end of the elongate retention member is configured to move substantially parallel to a longitudinal centerline of the support member when moved between its first location and its second location.

3. The apparatus of claim 1 wherein the first end of the second elongate retention member is configured to be moved from a third location in which the first end of the second elongate retention member is at a third distance from the second end of the second elongate retention member to a fourth location in which the first end of the second elongate retention member is at a fourth distance from the second end of the second elongate retention member, the third distance being greater than the fourth distance, and wherein at least a portion of the second elongate retention member is disposed at a second non-zero distance from an outer surface of the support member, and external thereto, when the first end of the second elongate retention member is at its fourth location.

4. The apparatus of claim 1, wherein the first distance is greater than the second distance.

5. A method, comprising:
disposing at least a portion of an implant having a longitudinal axis in a space between adjacent spinous processes such that the longitudinal axis extends perpendicular to a sagittal plane defined by the spinous processes, the implant having a support member, an actuator coupled to the support member, and an elongate retention member having a first end and a second end, the second end of the elongate retention member being fixed to one of the support member or the actuator;
rotating the actuator in a first direction about the longitudinal axis such that the first end of the elongate retention member moves relative to the second end of the elongate retention member in a direction substantially parallel to the longitudinal axis and the elongate retention member is moved to an expanded configuration;
wherein while rotating the actuator, a length of the implant measured along the longitudinal axis remains constant;
wherein when the elongate retention member is moved to the expanded configuration, at least a portion of the elongate retention member is moved through an opening in the support member and is disposed at a non-zero distance from, and external to, an outer surface of the support member.

6. The method of claim 5, wherein during the rotating, the first end of the elongate retention member is moved from a first location in which the first end of the elongate retention member is at a first distance from the second end of the elongate retention member to a second location in which the first end of the elongate retention member is at a second distance from the second end of the elongate retention member, the first distance being non-zero and greater than the second distance.

7. The method of claim 5, wherein during the rotating, the first end of the elongate retention member moves in a direction substantially parallel to a longitudinal centerline of the support member.

8. The method of claim 5:
wherein the elongate retention member is a first elongate retention member;
wherein the implant includes a second elongate retention member having a first end and a second end; the second end of the second elongate retention member being fixed to one of the support member or the actuator;
wherein during the rotating the first end of the second elongate retention member moves relative to the second end of the second elongate retention member and the second elongate retention member is moved to an expanded configuration.

9. An apparatus, comprising:
a support member configured to be disposed at least partially in a space between adjacent spinous processes;
an actuator assembly including a first portion, a second portion and an elongate member;
the first portion and the elongate member being moveably disposed at least partially within an interior region defined by the support member;
the second portion being disposed at a non-zero distance from the first portion;
the elongate member configured to be rotated relative to the support member and about an axis that extends substantially parallel to a centerline of the support member such that the first portion moves substantially parallel to the centerline of the support member in a first direction, the second portion moves substantially parallel to the centerline of the support member in a second direction opposite the first direction, and a retention portion of the apparatus is moved to an expanded configuration;
wherein in the expanded configuration, the retention portion extends through an opening in the support member such that a first section of the retention portion is disposed within an interior of the support member and a second section of the retention portion is disposed at a non-zero distance from, and external to, an outer surface of the support member;
wherein the apparatus has an overall length measured along the centerline which remains constant during rotation of the elongate member.

10. The apparatus of claim 9, wherein the retention portion is a first retention portion, the apparatus further comprising:
a second retention portion;
the first portion of the actuator assembly being configured to engage the first retention portion to move the first retention portion to its expanded configuration when the elongate member is rotated;
the second portion of the actuator assembly being configured to engage the second retention portion to move the second retention portion to an expanded configuration when the elongate member is rotated.

11. The apparatus of claim 9;
wherein the elongate member has first threaded portion including threads angled in a first direction and a second threaded portion including threads angled in a second direction opposite the first direction of the first threaded portion;
wherein the first portion of the actuator assembly being configured to threadedly engage the first threaded portion and move relative to the elongate member in the first longitudinal direction as the elongate member is rotated;
wherein the second portion of the actuator assembly being configured to threadedly engage the second threaded portion and move relative to the elongate member in the second longitudinal direction as the elongate member is rotated.

12. The apparatus of claim 9, wherein the retention portion includes a first end and a second end, the first end of the retention portion being fixedly coupled to the elongate member, the second end of the retention portion coupled to the first portion of the actuator assembly such that the second end of the retention portion moves with the first portion of the actuator assembly member relative to the elongate member as the elongate member is rotated.

* * * * *